(12) United States Patent
Kawachi et al.

(10) Patent No.: US 7,943,086 B2
(45) Date of Patent: May 17, 2011

(54) APPARATUS FOR WASHING AND DISINFECTING ENDOSCOPE BY USING DILUTED CHEMICALS

(75) Inventors: Shinichiro Kawachi, Tokyo (JP); Eiri Suzuki, Sagamihara (JP); Shintaro Suzuki, Tokyo (JP)

(73) Assignee: Olympus Medical Systems Corporation, Tokyo (JP)

( * ) Notice: Subject to any disclaimer, the term of this patent is extended or adjusted under 35 U.S.C. 154(b) by 441 days.

(21) Appl. No.: 12/109,508

(22) Filed: Apr. 25, 2008

(65) Prior Publication Data
US 2008/0267812 A1    Oct. 30, 2008

(30) Foreign Application Priority Data
Apr. 26, 2007    (JP) .................... 2007-117532

(51) Int. Cl.
*A61L 2/24*    (2006.01)
(52) U.S. Cl. .......................... 422/3; 422/559
(58) Field of Classification Search ............ 422/28, 422/3, 29, 62, 99, 102, 106, 500, 559; 134/113
See application file for complete search history.

(56) References Cited

FOREIGN PATENT DOCUMENTS

| | | |
|---|---|---|
| EP | 1 025 862 A2 | 8/2000 |
| EP | 1 815 782 A2 | 8/2007 |
| GB | 2 144 397 A | 3/1985 |
| GB | 2 379 173 A | 3/2003 |
| JP | 2000-287924 | 10/2000 |

OTHER PUBLICATIONS

Machine translation of JP 2000-287924 which has a publication date of Oct. 2000.*

* cited by examiner

*Primary Examiner* — Walter D Griffin
*Assistant Examiner* — Timothy Cleveland
(74) *Attorney, Agent, or Firm* — Scully, Scott, Murphy & Presser, P.C.

(57) ABSTRACT

An apparatus for washing and disinfecting an endoscope is provided. First and second chemicals and dilution water, which dilutes the chemicals to be used for disinfecting the endoscope, are charged into a tank. The tank includes a first portion, a second portion having an area of base smaller than that of the first portion, a first sensor detecting that the dilution water is charged into the first portion up to a first level, a second sensor detecting that the first chemical is charged into the second portion up to a second level, and a third sensor detecting that the second chemical is charged into the second portion up to a third level. A unit measures a first volume of the first chemical based on a result of the second sensor and measures a second volume of the second chemical based on results of the third sensor and the second sensor.

3 Claims, 13 Drawing Sheets

APPARATUS FOR WASHING AND DISINFECTING ENDOSCOPE BY USING DILUTED CHEMICALS

CROSS REFERENCE TO RELATED APPLICATION

The present application relates to and incorporates by reference Japanese Patent Application No. 2007-117532 filed on Apr. 26, 2007.

BACKGROUND OF THE INVENTION

1. Technical Field of the Invention

The present invention relates to an apparatus for washing and disinfecting an endoscope comprising a dilution tank into which a chemical, which is stored in a chemical bottle, and dilution water, which dilutes the chemical to a predetermined concentration to be used for disinfecting an endoscope, are charged.

2. Related Art

In recent years, endoscopes are widely used in medical and industrial fields. The endoscope used in the medical field comprises an elongated flexible insertion tube having an insertion duct for a therapeutic device (hereinafter, referred to as a "therapeutic device channel"). Inserting the insertion tube into a body cavity of an object (i.e., patient) being examined allows an operator to view organs in the body cavity and perform various treatments by using the therapeutic device inserted into the therapeutic device channel, as needed.

The endoscope in the medical field is used by being inserted into a body cavity, especially for the purpose of examination and treatment. Therefore, after use, the endoscope should be washed and disinfected for reuse. The method using an endoscope washer-disinfector is known as one method for washing and disinfecting a used endoscope.

The endoscope washer-disinfector automatically washes, disinfects, rinses, and drains (hereinafter, referred to as a "washing and disinfecting process") the used endoscope only by setting the endoscope in a washing bath. In this case, not only an outer surface of the endoscope but also a plurality of ducts (channels) such as an air duct, a water duct, and the therapeutic device channel therein are washed and disinfected.

In the meantime, when the endoscope washer-disinfector described above disinfects an endoscope, a disinfectant solution, for example, a chemical comprising a base solution such as peracetic acid and a buffer solution is used. The chemical is generally used by being diluted with dilution water such as tap water to a predetermined concentration. To ensure effective disinfection of the endoscope, it is required that adjustment of the concentration of dilution and control of humidity are properly performed.

In addition, when the diluted chemical is rapidly heated, it loses its efficacy. Therefore, when using a chemical having higher practical temperature, the dilution water is generally heated in a heating tank before it is charged into a dilution tank.

Furthermore, the conventional apparatus described above comprises two chemical bottles storing a base solution and a buffer solution having the volumes for disinfecting an endoscope one or more times, respectively. The base solution and the buffer solution in the respective chemical bottles are charged into the dilution tank. Thereafter, a predetermined volume of the dilution water is charged into the dilution tank through a dilution water inlet connected to the dilution tank to adjust the chemicals in a proper concentration. Note that the chemical properly diluted as described above is supplied from the dilution tank to the used endoscope by using a known means, thereby disinfecting the endoscope.

As described above, the chemical bottles store the base solution and the buffer solution for disinfecting the endoscopes several times. The base solution and the buffer solution are supplied from the respective chemical bottles to the dilution tank through respective supplying means, whose driving sources are pumps, provided in respective supply ducts connecting the chemical bottles to the dilution tank.

In addition, the volumes of the base solution and the buffer solution supplied to the dilution tank are generally controlled with water level sensors or the like disposed in the dilution tank or the respective chemical bottles. By way of example, Japan Pat. Appln. KOKAI Publication No. 2000-287924 discloses an endoscope washer-disinfector in which a plurality of level sensors are disposed in a tank. The level sensors detect the volume of a chemical stored in the tank in stages in response to the level of the chemical in the tank to control the volume of the chemical to be supplied.

In addition, an apparatus is known in which a base solution and a buffer solution are supplied from respective chemical bottles, in which the base solution and the buffer solution are stored for one-time disinfection of an endoscope, to a dilution tank. In this apparatus, a technique is well known for charging all the base solution and the buffer solution stored in the chemical bottles into the dilution tank using the weight of the base solution and the buffer solution.

However, in the endoscope washer-disinfector disclosed in the Japan Pat. Appln. KOKAI Publication No. 2000-287924, when the chemicals are diluted in the dilution tank, the volume of the chemicals to be used may be small with respect to the volume of the dilution tank. In such the case, that is, in a case where the chemicals are single-use, and the volume of the chemicals to be supplied is small, variation of the level in the dilution tank is small after the chemicals are supplied. Therefore, even when a plurality of level sensors are used, precise control of the volume of the chemicals to be supplied is difficult.

In addition, a configuration is known in which sensors detecting the level of a chemical are disposed inside a chemical bottle. In this case, replacement of the chemical bottle is complicated, while the chemical bottle becomes expensive. Furthermore, a technique is conceived in which the volume of chemicals to be supplied is controlled with flow sensors disposed in respective supply ducts connecting chemical bottles to a dilution tank. However, the flow sensor is expensive in general.

SUMMARY OF THE INVENTION

The present invention has been made in consideration of the foregoing conventional situation, and an object of the present invention is to provide an apparatus for washing and disinfecting an endoscope which has a relatively simple configuration manufactured at a low cost, accurately measures any volume of chemicals supplied to a dilution tank, and precisely controls the volume of the chemicals to be supplied.

In order to achieve the object, the present invention provides, as one aspect, an apparatus for washing and disinfecting an endoscope comprising: a dilution tank into which first and second chemicals and dilution water, which dilutes the first and second chemicals to a predetermined concentration to be used for disinfecting the endoscope, are charged, the dilution tank including: a first storage portion; a second storage portion which has an area of base smaller than an area of base of the first storage portion and communicates with the first storage portion; a first electrode sensor which detects a state in which the dilution water is charged into the second storage portion up to a first level; a second electrode sensor which detects a state in which the first chemical is charged into the second storage portion up to a second level; and a third electrode sensor which detects a state in which the second chemical is charged into the second storage portion up to a third level; and a measurement unit which measures, as a first volume, a volume of the first chemical based on a detection result of the second electrode sensor and measures, as a second volume, a volume of the second chemical based on a detection result of the third electrode sensor and the detection result of the second electrode sensor.

DETAILED DESCRIPTION OF THE PREFERRED EMBODIMENTS

Referring to the accompanying drawings, various embodiments of an apparatus for washing and disinfecting an endoscope according to the present invention will now be described.

First Embodiment

Figure 1:
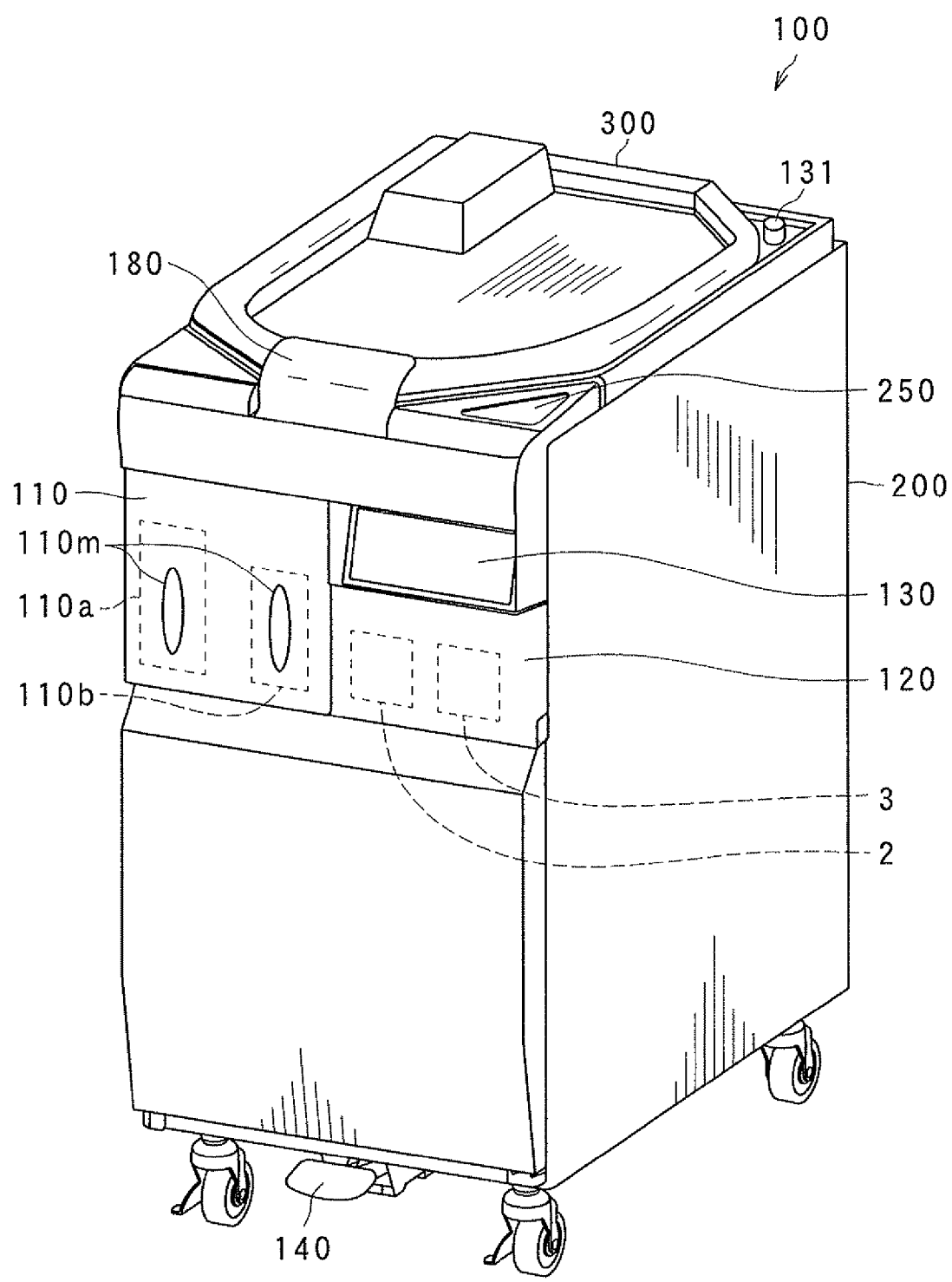
FIG. 1 is a perspective view of an endoscope washer-disinfector of the first embodiment according to the present invention.
Figure 2:
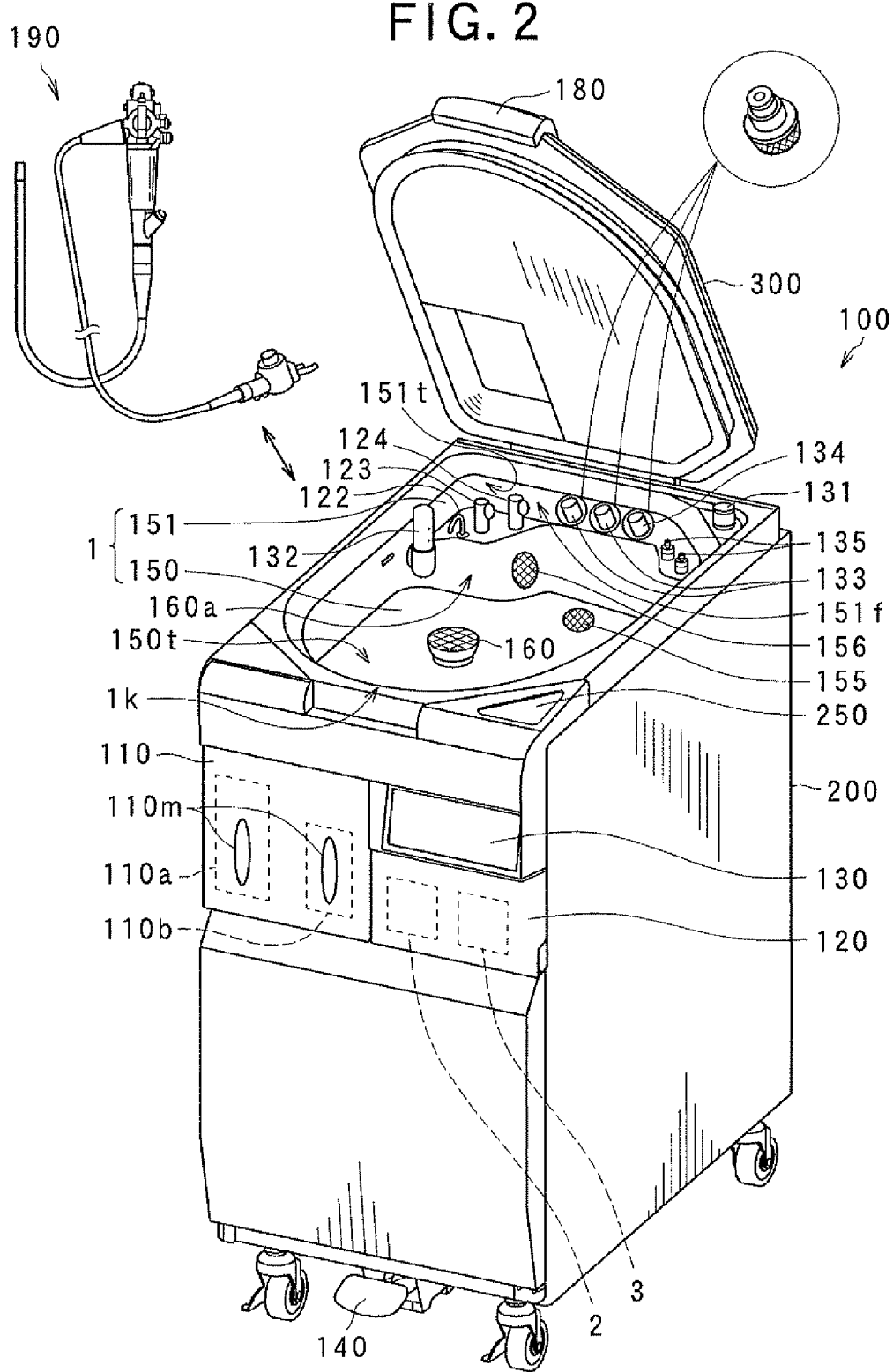
FIG. 2 is a perspective view of the endoscope washer-disinfector in which a top cover shown in FIG. 1 is opened and an endoscope can be accommodated in a washing and disinfection bath.

FIG. 1 is a perspective view of an endoscope washer-disinfector (endoscope reprocessor) of the first embodiment. FIG. 2 is a perspective view of an endoscope washer-disinfector showing a state where a top cover shown in FIG. 1 is opened and a washing and disinfection bath is capable of accommodating an endoscope.

An endoscope washer-disinfector 100 shown in FIGS. 1 and 2 is an apparatus for washing (cleaning) and disinfecting a used endoscope 190. The main part of the endoscope washer-disinfector 100 is comprised of a main body 200 and a top cover 300. The top cover 300 is a cover connected with the top of the main body 200 in an openable and closable state, for example, by hinges.

In FIG. 1, the top cover 300 is closed with respect to the main body 200. In this state, the top cover 300 is fixed to the main body 200 by a latch 180 provided on the top cover 300.

In the main body 200, a detergent/alcohol tray 110 is disposed at the upper portion of the front surface where an operator approaches (hereinafter, referred to as a "front surface"). The detergent/alcohol tray 110 can be drawn toward the front of the main body 200. The detergent/alcohol tray 110 accommodates a detergent tank 110a and an alcohol tank 110b. The detergent tank 110a stores a detergent which is a liquid used for washing an endoscope 190. The alcohol tank 110b stores alcohol which is a liquid used for drying the washed and disinfected endoscope 190. Since the detergent/alcohol tray 110 can be drawn toward the operator, each of the tanks 110 and 110b can be refilled with a predetermined liquid.

Two windows 110m, 110m are disposed on the detergent/alcohol tray 110. The operator can check the remaining amount of the detergent and the alcohol stored in the tanks 110 and 110b through the windows 110m, 110m, respectively. The detergent is a concentrated one and is diluted with tap water, which is filtered through a feed water filter (not shown), to a predetermined concentration. In the first embodiment, hereinafter, a mixed solution of the detergent and the tap water is referred to as a "washing solution".

In addition, in the main body 200, a cassette tray 120 is disposed at the upper right portion of the front surface. The cassette tray 120 can be drawn toward the front of the main body 200. The cassette tray 120 accommodates a chemical bottle 2 and a chemical bottle 3. The chemical bottle 2 stores a base solution, which is a chemical such as peracetic acid, of a disinfectant solution. The disinfectant solution is used for disinfecting the endoscope 190. The chemical bottle 3 stores a buffer solution of the disinfectant solution Since the cassette tray 120 can be drawn forward, each of the chemical bottles 2 and 3 can be refilled with a predetermined liquid.

Furthermore, a sub-operation panel 130 is disposed above the cassette tray 120 at the front surface of the main body 200. The sub-operation panel 130 has a display, which displays washing time and disinfection time, an instruction button for heating the disinfectant solution, and the like. In addition, a pedal switch 140 is provided below the front surface of the main body 200. When the operator depresses the pedal switch 140, the top cover 300 which was closed at the top of the main body 200 opens upward from the main body 200 as shown in FIG. 2.

In addition, on the top surface of the main body 200 shown in FIG. 2, main operation panels 250 are disposed at the both ends of the front surface side where the operator approaches. The main operation panels 250 comprise setting switches such as a washing/disinfection start switch and a washing/disinfection mode selection switch.

In addition, on the top surface of the main body 200, a feed-water hose connector 131 is provided on the back surface side opposite to the front surface side where the operator approaches. Tap water is supplied to the main body 200 through the feed-water hose connector 131. A feed-water hose connected with a faucet (not shown) is connected to the feed-water hose connector 131. Note that the feed-water hose connector 131 may be provided with a mesh filter through which the tap water is filtered.

In addition, a washing and disinfection bath 1 which is capable of accommodating the endoscope 190 is provided at a substantially central portion of the top surface of the main body 200. An accommodating space for an endoscope of the washing and disinfection bath 1 is opened and closed by the top cover 300. The washing and disinfection bath 1 comprises a bath body 150 and a terrace portion 151 which is continuously formed along the outer edge of the accommodating space of the bath body 150.

The bath body 150 accommodates the used endoscope 190 when it is washed and disinfected. A first outlet 155 is provided in the bottom surface 150t, which is a surface of the bath body 150. The first outlet 155 discharges a washing solution, water, alcohol, a disinfectant solution, and the like supplied to the bath body 150.

In addition, a circulation vent 156 is provided at an arbitrary position in a circumferential side surface 150s, which is a surface in the bath body 150. The circulation vent 156 supplies a washing solution, water, a disinfectant solution, and the like supplied to the bath body 150 to ducts which are provided inside the endoscope 190 via a predetermined means (not shown). Alternatively, the circulation vent 156 resupplies the washing solution, water, disinfectant solution, and the like from a feed-water circulation nozzle 124 to the bath body 150 through a mesh filter or the like. Note that the circulation vent 156 may be provided with a mesh fitter through which the washing solution and the like are filtered.

Note that the circulation vent 156 described above may be provided in the bottom surface 150t of the bath body 150. Providing the circulation vent 156 at the bottom surface 150t of the bath body 150 accelerates the timing of supplying the washing solution, water, disinfectant solution, and the like to the ducts of the endoscope 190 or the timing of resupplying them to the bath body 150. Furthermore, providing the circulation vent 156 at the bottom surface makes it easy for the operator to approach the circulation vent 156 to replace the mesh filter or the like provided in the circulation vent 156.

A washing case 160 is provided at a substantially central portion of the bottom surface 150t of the bath body 150 of the washing and disinfection bath 1. The washing case 160 accommodates buttons such as scope switches of the endoscope 190 and detachable components mounted on the endoscope 190. In consequence, the buttons and the detached components are washed and disinfected together with the endoscope 190.

A level sensor 132 with a cover is provided at an arbitrary position on the side surface 150s of the bath body 150. The level sensor 132 detects levels of the washing solution, water, disinfectant solution, and the like supplied to the bath body 150.

A detergent nozzle 122 and a disinfectant solution nozzle 123 are disposed on a surface of the terrace portion 151. The surface is different from the terrace surface 151t and is parallel to the bottom surface 150t of the bath body 150. The detergent nozzle 122 supplies a washing solution supplied from the detergent tank 110a to the bath body 150 by using a pump (not shown). The washing solution is diluted with tap water to a predetermined concentration. The disinfectant solution nozzle 123 supplies a disinfectant solution, which is supplied from a dilution tank 6 described below (refer to FIG. 3), by using a pump 8 described below (refer to FIG. 3).

Furthermore, the feed-water circulation nozzle 124 is disposed on the surface of the terrace portion 151. The surface is parallel to the bottom surface 150t of the bath body 150. The feed-water circulation nozzle 124 supplies water to the bath body 150 or resupplies the washing solution, water, disinfectant solution, and the like drawn through the circulation vent 156 of the bath body 150 by suction.

Note that the detergent nozzle 122, the disinfectant solution nozzle 123, and the feed-water circulation nozzle 124 may be disposed on the terrace surface 151t.

In addition, on the terrace surface 151t of the terrace portion 151, a plurality of ports (two ports are shown in FIG. 2) including a port 133 for supplying air and water and for a forceps hole, a port 134 for raising the forceps, and a port 135 for detecting water leaks are provided on a surface 151f opposite to a position 1k where the operator approaches. The port 133 supplies a washing solution, water, alcohol, a disinfectant solution, air, or the like to ducts which are provided inside the endoscope 190.

Next, the internal configuration of the above described endoscope washer-disinfector will be described with reference to FIGS. 3 to 5, focusing on the above described chemical bottles 2 and 3 and the dilution tank 6.

Figure 3:
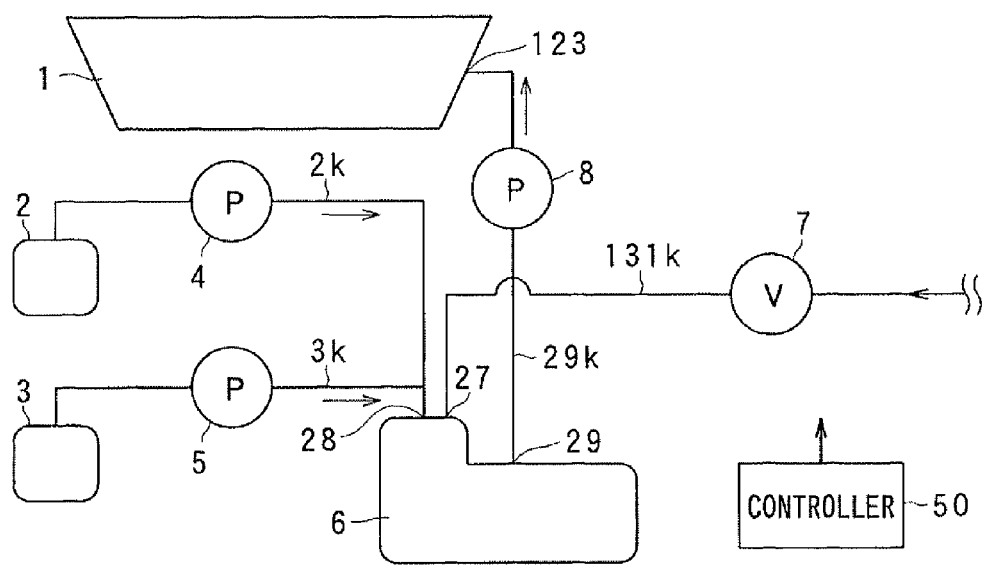
FIG. 3 is a schematic view showing a configuration of duct lines used in a disinfectant solution supplying mechanism in the endoscope washer-disinfector shown in FIG. 1.

FIG. 3 is a schematic view of duct lines used in a disinfectant solution supplying mechanism in the endoscope washer-disinfector shown in FIG. 1. FIG. 4 is a schematic view showing a configuration of the dilution tank shown in FIG. 3. FIG. 5 is a top view of the dilution tank shown in FIG. 4.

As shown in FIG. 3, the chemical bottles 2 and 3 accommodated in the cassette tray 120 are connected to a chemical inlet 28 provided on the dilution tank 6 through ducts 2k and 3k, respectively. Pumps 4 and 5 are provided at the midpoints of the ducts 2k and 3k, respectively. The pumps 4 and 5 charge the base solution and the buffer solution of the disinfectant solution from the chemical bottles 2 and 3 into the dilution tank 6, respectively.

In addition, a duct 131k extending from the above described feed-water hose connector 131 is connected with a feed-water port 27 of the dilution tank 6. A dilution valve 7 is provided at the midpoint of the duct 131k. Opening the dilution valve 7 charges the dilution water such as tap water to the dilution tank 6, and closing the dilution valve 7 stops charging the dilution water.

Furthermore, a chemical outlet 29, which is provided on the dilution tank 6, is connected to the disinfectant solution nozzle 123 of the washing and disinfection bath 1 through a duct 29k. The pump 8 is provided at the midpoint of the duct 29k. Driving the pump 8 supplies the diluted disinfectant solution stored in the dilution tank 6 to the washing and disinfection bath 1.

Figure 4:
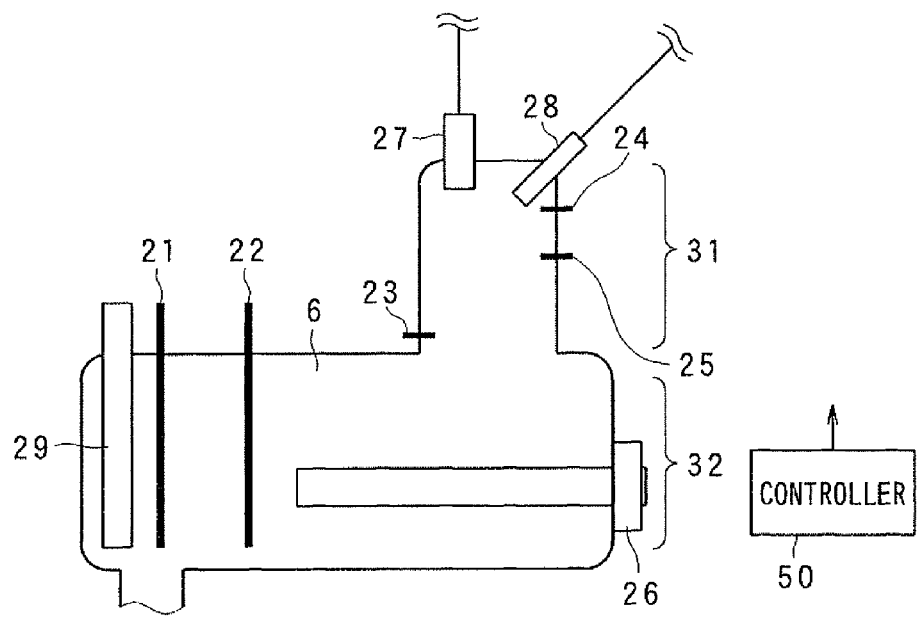
FIG. 4 is a schematic view showing the configuration of the dilution tank shown in FIG. 3.
Figure 5:
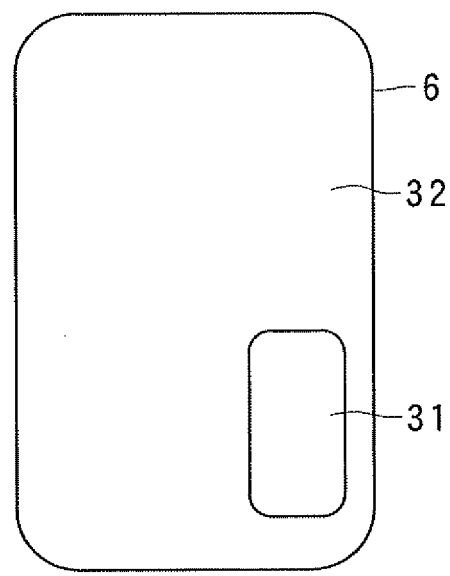
FIG. 5 is a top view of the dilution tank shown in FIG. 4.

As shown in FIGS. 4 and 5 the main part of the dilution tank 6 comprises a first storage portion 32 and a second storage portion 31. The second storage portion 31 is formed on the top of the first storage portion 32 and communicates with the first storage portion 32. The second storage portion 31 has an area of base and a volume smaller than those of the first storage portion 32. That is, the dilution tank 6 comprises a two-stage storage portion having two different volumes.

The first storage portion 32 is provided with not only the above described chemical outlet 29 but also an electrode sensor 21 connected to ground, a temperature sensor 22, and a heater 26 which is a heating member.

The temperature sensor 22 measures the temperature of the dilution water charged into the first storage portion 32. The heater 26 heats the dilution water to the preset temperature, which is a practical temperature of, for example, between 40° C. and 50° C. (degrees). The reason that the dilution water is heated to the practical temperature before the chemicals are diluted is that rapidly heating the chemicals accelerates degradation of the chemicals. Note that, instead of using the heater 26, the dilution water may be previously heated to the practical temperature before it is supplied to the dilution tank 6. As described above, heating the dilution water to the practical temperature before diluting the chemicals prevents the chemicals from degrading and allows the mixed chemicals to be rapidly heated.

The second storage portion 31 is provided with not only the above described feed-water port 27 and chemical inlet 28 but also a first electrode sensor 23, a second electrode sensor 25, and a third electrode sensor 24.

The feed-water port 27 and the chemical inlet 28 are provided on the top of the second storage portion 31. The first electrode sensor 23 is provided in the vicinity of the position where the second storage portion 31 communicates with the first storage portion 32. The second electrode sensor 25 is provided at a position higher than that of the first electrode sensor 23. The difference between the height (longitudinal installation position) of the first electrode sensor 23 and the height (longitudinal installation position) of the second electrode sensor 25 corresponds to the height (level) of the base solution in the second storage portion 31. Note that the dilution water is charged into the dilution tank 6 until the first electrode sensor 23 detects the dilution water. Next, the base solution is charged from the chemical bottle 2 into the second storage portion 31. The third electrode sensor 24 is provided at a position higher than that of the second electrode sensor 25. The difference between the height (longitudinal installation position) of the second electrode sensor 25 and the height of the third electrode sensor 24 corresponds to the height (level) of the buffer solution in the second storage portion 31. Note that the base solution is charged into the dilution tank 6 until the second electrode sensor 25 detects the base solution. Next, the buffer solution is charged from the chemical bottle 3 into the second storage portion 31.

The first electrode sensor 23 detects a state in which the dilution water is charged into the first storage portion 32 in the range from the bottom of the dilution tank 6 to the height of the first electrode sensor 23. That is, the first electrode sensor 23 detects a state in which the dilution water has reached a first level at which the first storage portion 32 is filled with the dilution water. The first electrode sensor 23 sends the obtained detection result to a controller (CPU, measurement unit) 50.

The second electrode sensor 25 detects a state in which the base solution is charged from the chemical bottle 2 into the second storage portion 31 in the range from the height of the first electrode sensor 23 to the height of the second electrode sensor 25. That is, the second electrode sensor 25 detects a state in which the base solution has reached a second level higher than the first level. In other words, the second electrode sensor 25 detects a state in which the diluted base solution is stored up to the second level. The second electrode sensor 25 sends the obtained detection result to the controller 50. The controller 50 determines a first volume of the base solution by calculating the difference between the second level and the first level.

The third electrode sensor 24 detects a state in which the buffer solution is charged from the chemical bottle 3 into the second storage portion 31 in the range from the height of the second electrode sensor 25 to the height of the third electrode sensor 24. That is, the third electrode sensor 24 detects a state in which the buffer solution has reached a third level higher than the second level. In other words, the third electrode sensor 24 detects a state in which the diluted base solution and buffer solution are stored up to the third level. The third electrode sensor 24 sends the obtained detection result to the controller 50. The controller 50 determines a second volume of the buffer solution by calculating the difference between the third level and the second level.

Figure 6:
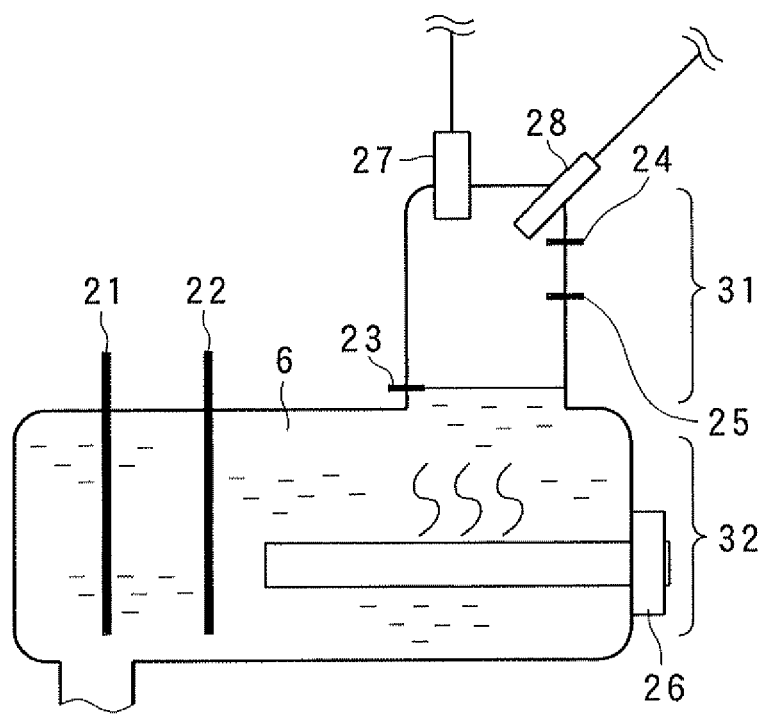
FIG. 6 is a view showing a state in which dilution water is stored up to a first level in the dilution tank shown in FIG. 4.
Figure 7:
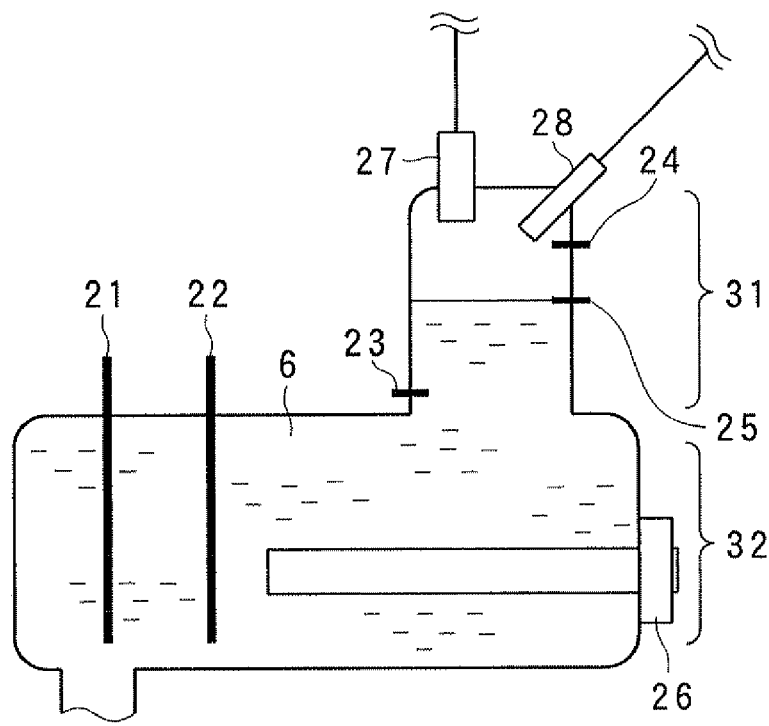
FIG. 7 is a view showing a state in which a base solution diluted with the dilution water is stored up to a second level in the dilution tank shown in FIG. 4.
Figure 8:
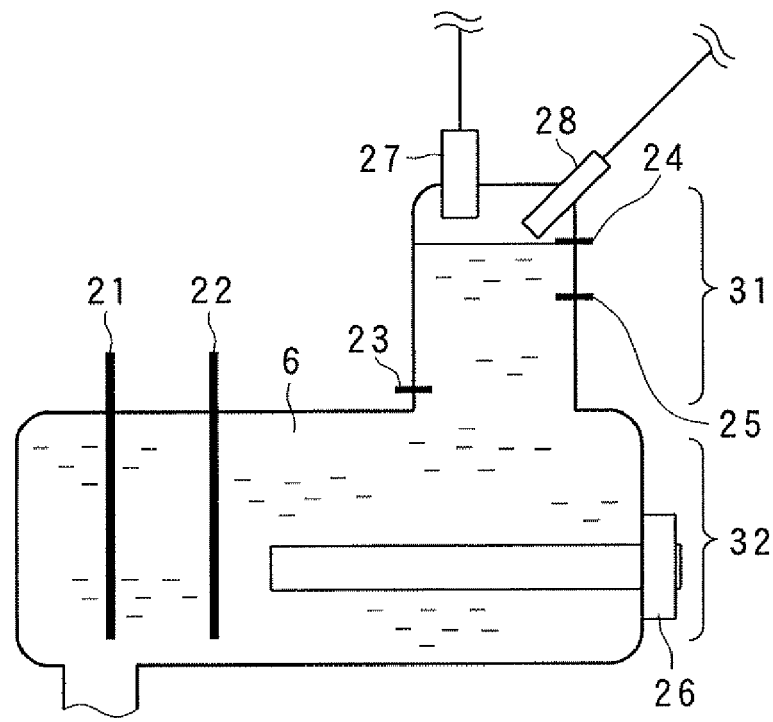
FIG. 8 is a view showing a state in which the base solution and a buffer solution diluted with the dilution water are stored up to a third level in the dilution tank shown in FIG. 4 and mixture of the chemicals is completed.

Next, the operation of the endoscope washer-disinfector 100 of the first embodiment will be described with reference to FIGS. 6 to 8. FIG. 6 shows a state in which the dilution water is stored up to the first level in the dilution tank 6 shown in FIG. 4. FIG. 7 shows a state in which the base solution diluted with the dilution water is stored up to the second level in the dilution tank 6 shown in FIG. 4. FIG. 8 shows a state in which the base solution and buffer solution diluted with the dilution water are stored up to the third level in the dilution tank 6 shown in FIG. 4 and the mixture of the chemicals is completed.

Hereinafter, a process will be described in which the dilution water and both of the base solution and the buffer solution, which are chemicals to be a disinfectant solution, are charged into the dilution tank 6 of the endoscope washer-disinfector 100. Note that descriptions of well-known operations of the endoscope washer-disinfector will be omitted.

First, in order to mix the chemicals to prepare a disinfectant solution, the controller 50 of the endoscope washer-disinfector 100 opens the dilution valve 7 (refer to FIG. 3). In consequence of this, the dilution water such as tap water is charged from the feed-water port 27 into the dilution tank 6. As a result of the charge, as shown in FIG. 6, the dilution water is stored in the first storage portion 32 and the second storage portion 31 up to the first level which is the height of the first electrode sensor 23. Thereby, the first electrode sensor 23 sends a detection signal to the controller 50. Upon receiving the detection signal, the controller 50 sends a control signal for closing the dilution valve 7.

In this case, when the temperature sensor 22 detects a state in which the temperature of the dilution water stored in the first storage portion 32 is lower than a practical temperature of, for example, between 40° C. and 50° C., the controller 50 controls the drive of the heater 26 to heat the dilution water to the practical temperature. Note that the dilution water may be heated to the practical temperature before it is charged into the dilution tank 6.

Next, the controller 50 drives the pump 4 to charge the base solution stored in the chemical bottle 2 into the dilution tank 6 through the chemical inlet 28. As a result of the charge, as shown in FIG. 7, the base solution diluted with the dilution water is stored in the second storage portion 31 up to the second level which is the height of the second electrode sensor 25. Thereby, the second electrode sensor 25 sends a detection signal to the controller 50. Upon receiving the detection signal, the controller 50 sends a control signal for stopping the drive of the pump 4. In this case, the controller 50 determines a first volume of the base solution by calculating the difference between the second level and the first level.

Next, the controller 50 drives the pump 5 to charge the buffer solution stored in the chemical bottle 3 into the dilution tank 6 through the chemical inlet 28. As a result of the charge, as shown in FIG. 8, the base solution and buffer solution diluted with the dilution water are stored in the second storage portion 31 up to the third level which is the height of the third electrode sensor 24. Thereby, the third electrode sensor 24 sends a detection signal to the controller 50. Upon receiving the detection signal, the controller 50 sends a control signal for stopping the drive of the pump 5. In this case, the controller 50 determines a second volume of the buffer solution by calculating the difference between the third level and the second level.

Note that the base solution and buffer solution diluted with the dilution water, which are detected by the third electrode sensor 24, are mixed to be a disinfectant solution in a predetermined concentration used for disinfecting the endoscope 190. Note that the base solution and buffer solution diluted with the dilution water may be heated by the heater 26.

Finally, the controller 50 controls the drive of the pump 8 to supply the disinfectant solution in a predetermined concentration from the chemical outlet 29 to the washing and disinfection bath 1 through the duct 29k.

As described above, in the first embodiment, the main part of the dilution tank 6 comprises the first storage portion 32 and the second storage portion 31 which is formed on the top of the first storage portion 32 and has an area of base and a volume smaller than those of the first storage portion 32. That is, the dilution tank 6 comprises a two-stage storage portion having two different volumes.

In addition, the second storage portion 31 which has an area of base and a volume smaller than those of the first storage portion 32 is provided with the second electrode sensor 25 for determining the first volume of the base solution and the third electrode sensor 24 for determining the second volume of the buffer solution. That is, the volumes of the base solution and the buffer solution are measured in the second storage portion 31.

According to the above configuration, even when the volume of the base solution charged into the dilution tank 6 is small, since the area of base and the volume of the second storage portion 31 are smaller than those of the first storage portion 32, variation of the level in the second storage portion 31 caused by charging the base solution becomes relatively large. Therefore, even after diluting with dilution water, the second electrode sensor 25 can accurately detect the second level after the base solution is charged. In consequence, the first volume, which is the volume of the charged base solution, can be accurately measured with a relatively simple configuration manufactured at a low cost by using the second electrode sensor 25 only.

In addition, even when the volume of the buffer solution charged into the dilution tank 6 is small, since the area of base and the volume of the second storage portion 31 are smaller than those of the first storage portion 32, variation of the level in the second storage portion 31 caused by charging the buffer solution becomes relatively large. Therefore, even after diluting with dilution water, the third electrode sensor 24 can accurately detect the third level after the buffer solution is charged. In consequence, the second volume, which is the volume of the charged buffer solution, can be accurately measured with a relatively simple configuration manufactured at a low cost by using the third electrode sensor 24 only.

As described above, the endoscope washer-disinfector 100 can be provided which accurately measures any volume of chemicals supplied to the dilution tank 6 and precisely controls the volume of the chemicals to be supplied. The endoscope washer-disinfector 100 has a configuration manufactured at a low cost in which only conventional electrode level sensors are disposed in the second storage portion 31 of the dilution tank 6. That is, the configuration does not require disposing sophisticated and precise level sensors in the dilution tank 6 or the chemical bottles 2, 3 and disposing flow sensors in the ducts 2k and 3k.

Figure 9:
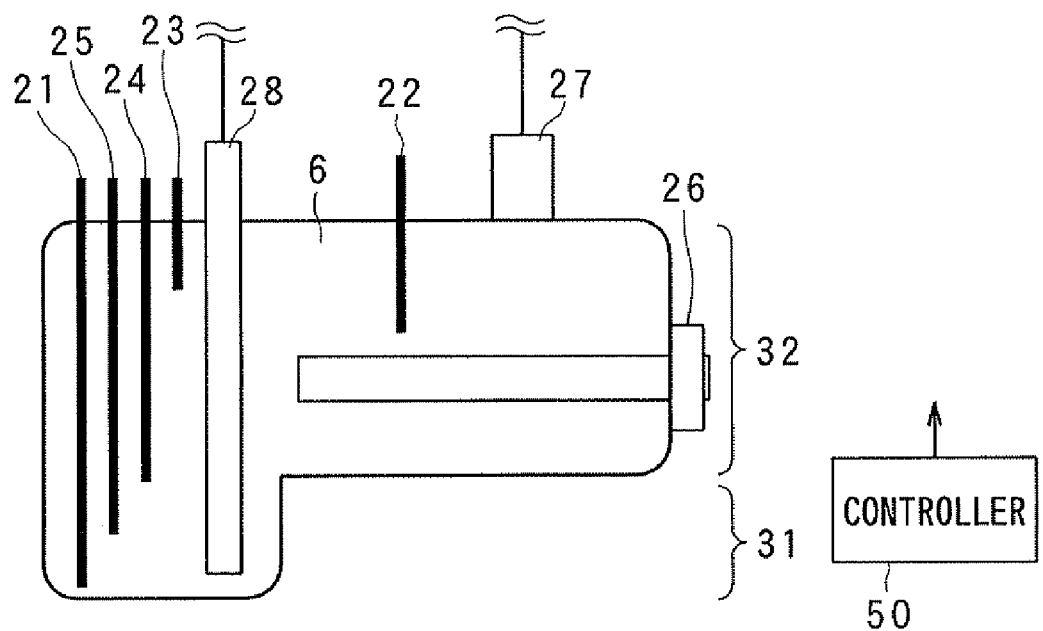
FIG. 9 is a view showing a modification example of the configuration of the dilution tank of the endoscope washer-disinfector according to the first embodiment.
Figure 10:
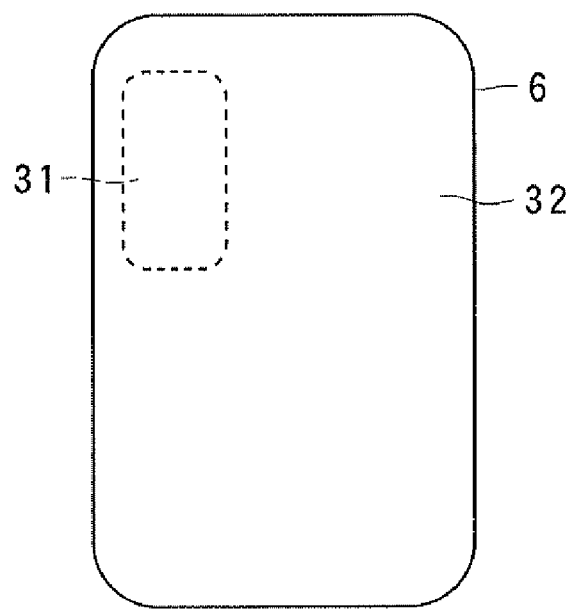
FIG. 10 is a top view of the dilution tank shown in FIG. 9.

Hereinafter, a modification example will be described with reference to FIGS. 9 and 10. FIG. 9 is a view showing a modification example of the configuration of the dilution tank of the endoscope washer-disinfector of the first embodiment. FIG. 10 is a top view of the dilution tank shown in FIG. 9.

In the above described first embodiment, the main part of the dilution tank 6 comprises the first storage portion 32 and the second storage portion 31 which is formed on the top of the first storage portion 32 and has an area of base and a volume smaller than those of the first storage portion 32. However, the configuration of the dilution tank 6 is not limited to the above described one. As shown in FIGS. 9 and 10, the dilution tank 6 may comprises a two-stage storage portion configured by forming the second storage portion 31 on the underside of the first storage portion 32. The second storage portion 31 is communicated with the first storage portion 32 and has an area of base and a volume smaller than those of the first storage portion 32.

The feed-water port 27 is provided on the top of the first storage portion 32. The chemical inlet 28 is provided so as to open into the second storage portion 31. The electrode sensor 21 is provided so as to be positioned in the second storage portion 31. The second electrode sensor 25 is disposed above the bottom of the second storage portion 31 in the second storage portion 31. The distance between the bottom of the second storage portion 31 and the second electrode sensor 25 corresponds to the height of the base solution in the second storage portion 31 charged from the chemical bottle 2. The third electrode sensor 24 is provided at the position higher than that of the second electrode sensor 25. The difference between the height of the second electrode sensor 25 and the height of the third electrode sensor 24 corresponds to the height of the buffer solution in the second storage portion 31. Note that the base solution is charged into the second storage portion 31 until the second electrode sensor 25 detects the base solution. Next, the buffer solution is charged from the chemical bottle 3 into the second storage portion 31.

The first electrode sensor 23 is provided at the position higher than that of the third electrode sensor 24 in the first storage portion 32. The difference between the height of the third electrode sensor 24 and the height of the first electrode sensor 23 corresponds to the height of the dilution water in the first storage portion 32. Note that the buffer solution is charged into the second storage portion 31 until the third electrode sensor 24 detects the buffer solution. Next, the dilution water is charged into the first storage portion 32.

In this case, the second electrode sensor 25 detects a state in which the base solution is charged from the chemical bottle 2 into the second storage portion 31 in the range from the bottom thereof to the height of the second electrode sensor 25. That is, the second electrode sensor 25 detects a state in which the base solution has reached the second level The second electrode sensor 25 sends the obtained detection result to a controller 50. The controller 50 determines a first volume of the base solution based on the detection result.

The third electrode sensor 24 detects a state in which the buffer solution is charged from the chemical bottle 3 into the second storage portion 31 up to the height of the third electrode sensor 24. That is, the third electrode sensor 24 detects a state in which the buffer solution has reached the third level higher than the second level. In other words, the third electrode sensor 24 detects a state in which the base solution and the buffer solution are stored up to the third level. The third electrode sensor 24 sends the obtained detection result to the controller 50. The controller 50 determines a second volume of the buffer solution by calculating the difference between the third level and the second level.

The first electrode sensor 23 detects a state in which the dilution water is charged into the first storage portion 32 up to the height of the first electrode sensor 23. That is, the first electrode sensor 23 detects a state in which the dilution water has reached the first level higher than the third level. In other words, the first electrode sensor 23 detects a state in which the diluted base solution and buffer solution are stored up to the first level. The first electrode sensor 23 sends the obtained detection result to the controller 50.

The mixture of the chemicals using the above described endoscope washer-disinfector is performed by the process different from that of the first embodiment. First, the first volume of the base solution is measured in the second storage portion 31. Next, the second volume of the buffer solution is measured in the second storage portion 31. Finally, the base solution and the buffer solution are diluted with the dilution water in the first storage portion 32. The configuration and the operation described above provide the same advantages as those of the first embodiment.

Second Embodiment

Figure 11:
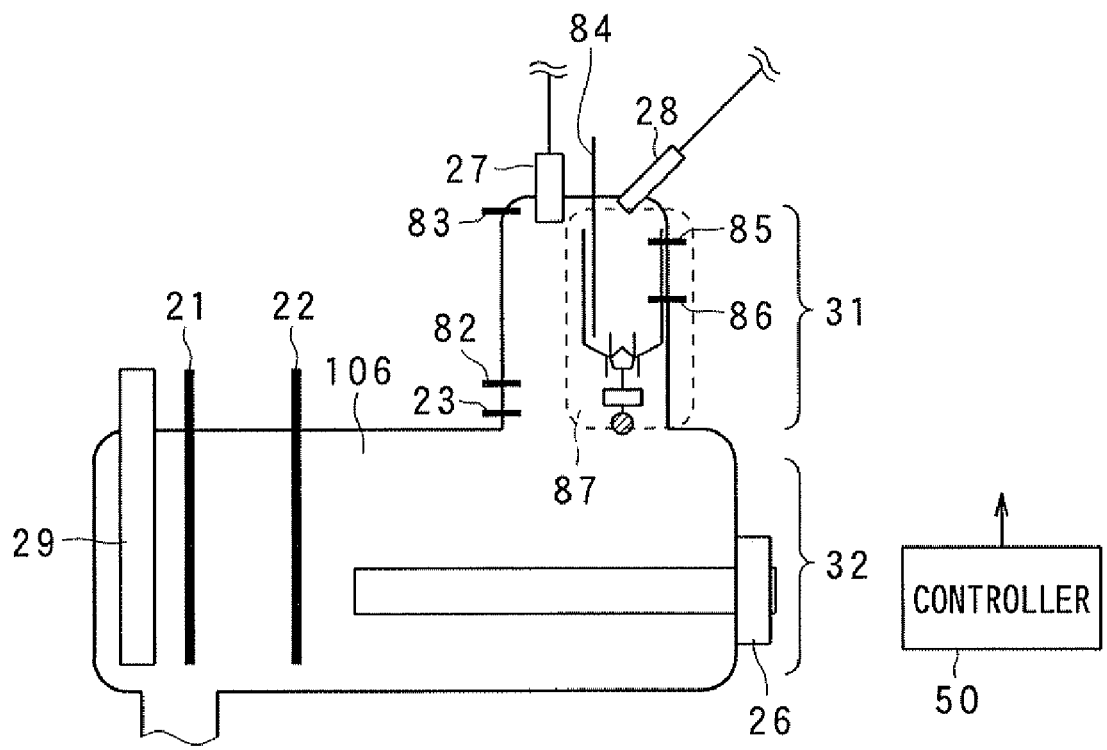
FIG. 11 is a schematic view showing a configuration of a dilution tank of an endoscope washer-disinfector of the second embodiment according to the present invention.
Figure 12:
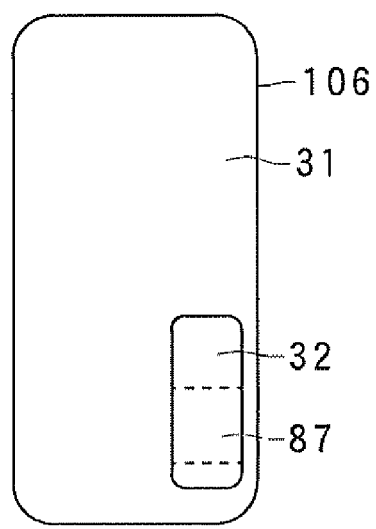
FIG. 12 is a top view of the dilution tank shown in FIG. 11.
Figure 13:
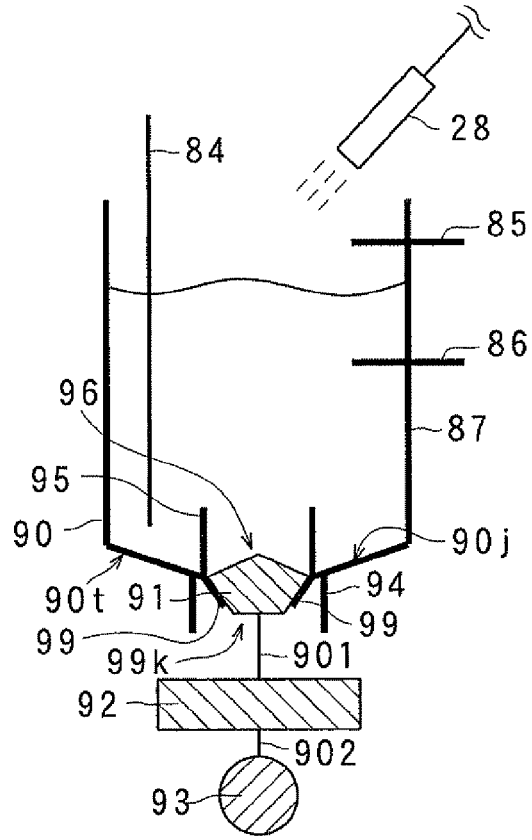
FIG. 13 is a schematic view showing a configuration of a metering cup provided in a second storage portion of the dilution tank shown in FIG. 11.
Figure 14:
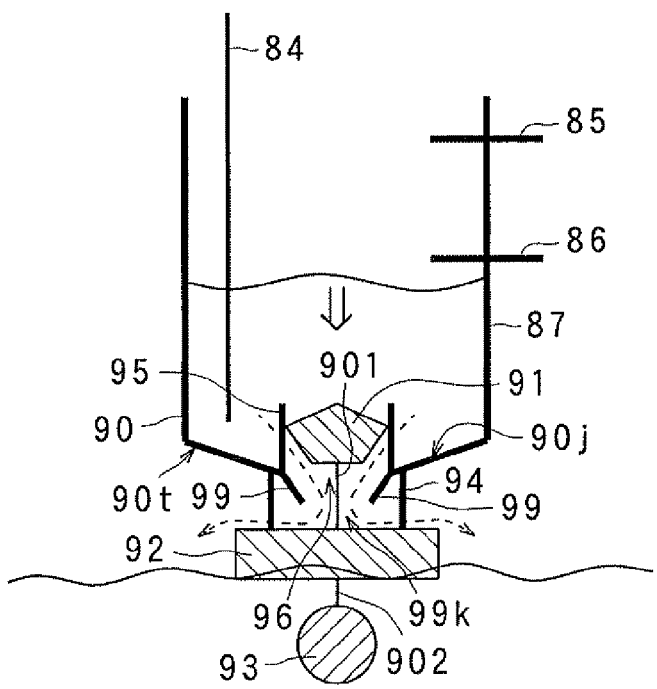
FIG. 14 is a view showing a state where an outlet of the metering cup shown in FIG. 13 is opened.
Figure 15:
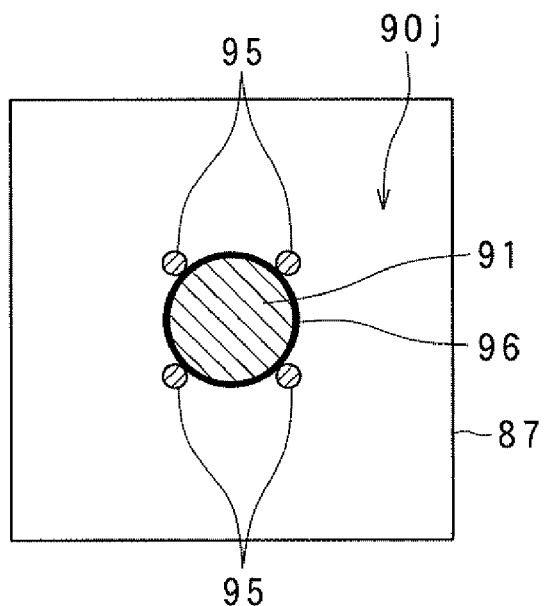
FIG. 15 is a top view of the metering cup shown in FIG. 13.
Figure 16:
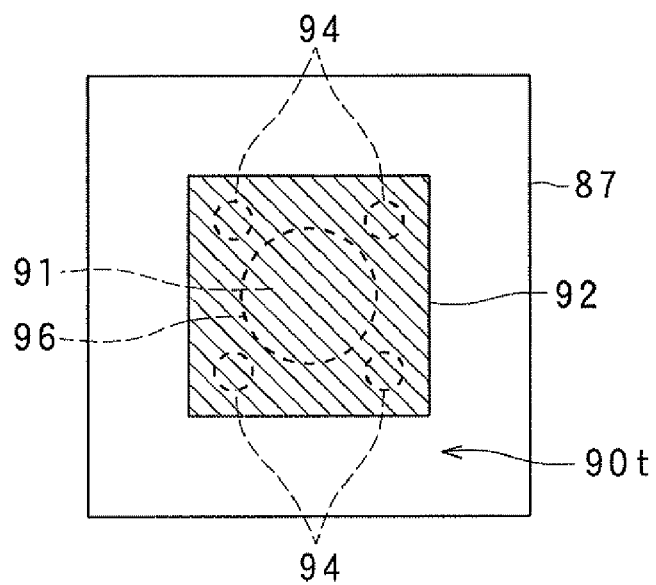
FIG. 16 is a bottom view of the metering cup shown in FIG. 13.

FIG. 11 is a schematic view showing a configuration of a dilution tank of an endoscope washer-disinfector of the second embodiment. FIG. 12 is a top view of the dilution tank shown in FIG. 11. FIG. 13 is a schematic view showing a configuration of a metering cup provided in the second storage portion of the dilution tank shown in FIG. 11. FIG. 14 is a view showing a state where an outlet of the metering cup shown in FIG. 13 is opened. FIG. 15 is a top view of the metering cup shown in FIG. 13. FIG. 16 is a bottom view of the metering cup shown in FIG. 13.

The configuration of the endoscope washer-disinfector of the second embodiment differs from that of the first embodiment shown in FIGS. 1 to 8 in that the metering cup, which measures the volume of the charged base solution and buffer solution, is provided in the second storage portion. Therefore, only the difference from the first embodiment will be described. The same parts as those of the first embodiment are denoted with the same reference numerals to omit descriptions of the parts.

As shown in FIGS. 11 and 12, the main part of the dilution tank 106 comprises the first storage portion 32 and the second storage portion 31. The second storage portion 31 is formed on the top of the first storage portion 32 and is communicated with the first storage portion 32. The second storage portion 31 has an area of base and a volume smaller than those of the first storage portion 32. That is, in the second embodiment, the dilution tank 106 comprises a two-stage storage portion having two different volumes.

The second storage portion 31 is provided with not only the above described feed-water port 27, chemical inlet 28, and first electrode sensor 23 but also a sixth electrode sensor 82, a seventh electrode sensor 83, and a metering cup 87 which is a metering cup member.

The sixth electrode sensor 82 is provided on a location guide (not shown) disposed slightly above the first electrode sensor 23 in the second storage portion 31. The seventh electrode sensor 83 is provided above the sixth electrode sensor 82 and in the vicinity of the top of the second storage portion 31 in the second storage portion 31.

The sixth electrode sensor 82 detects a state in which either the dilution water or the base solution and buffer solution diluted with the dilution water are stored in the second storage portion 31 up to the height (longitudinal installation position) of the sixth electrode sensor 82. That is, the sixth electrode sensor 82 detects a state in which either the dilution water or the base solution and buffer solution diluted with the dilution water have reached a sixth level higher than the first level. The sixth electrode sensor 82 sends the obtained detection result to the controller 50.

In addition, the seventh electrode sensor 83 detects a state in which either the dilution water or the base solution and buffer solution diluted with the dilution water are stored in the second storage portion 31 up to the height (longitudinal installation position) of the seventh electrode sensor 83. That is, the seventh electrode sensor 83 detects a state in which either the dilution water or the base solution and buffer solution diluted with the dilution water have reached a seventh level higher than the sixth level. The seventh electrode sensor 83 sends the obtained detection result to the controller 50.

As shown in FIGS. 11 and 13, the top of the metering cup 87 is opened in the second storage portion 31. More specifically, the top of the metering cup 87 is opened toward the chemical inlet 28.

As shown in FIG. 13, an outlet 96 is formed in a bottom portion 90 of the metering cup 87. The outlet 96 is provided with a detachable stopper member 91. In addition, a retainer 99 is formed along the outer circumference of the outlet 96 in a lower surface 90*t* of the bottom portion 90. The retainer 99 is a retaining member for preventing the stopper member 91 from being pulled out from the outlet 96 to the outside of the metering cup 87. The retainer 99 has an opening 99*k*.

A float member 92 is connected to the bottom portion of the stopper member 91 through a first linear member 901. The float member 92 is made of a member whose specific gravity is less than that of either the dilution water or the base solution and buffer solution diluted with the dilution water. Therefore, when either the dilution water or the base solution and buffer solution diluted with the dilution water are stored up to the sixth level, at which the sixth electrode sensor 82 detects them, the float member 92 floats. In consequence, as shown in FIG. 14, the stopper member 91 floats together with the float member 92 and the first linear member 901, thereby opening the outlet 96.

A weight 93, which is a load member, is connected to the bottom portion of the float member 92 through a second linear member 902. The weight 93 pulls the stopper member 91 downward through the second linear member 902, the float member 92, and the first linear member 901 to bring the stopper member 91 into contact with the retainer 99 by its load, thereby closing the outlet 96.

In a state as shown in FIG. 16, which is a bottom view, float member position restricting guides 94 are provided at four positions, which surround the outlet 96, on the lower surface 90t of the bottom portion 90 of the metering cup 87. The float member position restricting guides 94 extend below the retainer 99. The float member 92 floating in either the dilution water or the base solution and buffer solution diluted with the dilution water comes into contact with the float member position restricting guides 94 below the retainer 99, thereby preventing the float member 92 from closing the opening 99k of the retainer 99.

In a state as shown in FIG. 15, which is a top view, stopper member position restricting guides 95 are provided at four positions, which surround the outlet 96, on the upper surface 90j of the bottom portion 90 of the metering cup 87. The stopper member position restricting guides 95 stand on the upper surface 90j. When the float member 92 comes into contact with the float member position restricting guides 94, the stopper member 91 is raised, and the height of the stopper member position restricting guides 95 is greater than the height (longitudinal position) of the stopper member 91. Thereby, when the stopper member 91 is raised, the stopper member position restricting guides 95 defines the position of the stopper member 91 with respect to the outlet 96. That is, the position of the stopper member 91 falls inside the stopper member position restricting guides 95 as shown in FIG. 15 and is defined so as not to fall outside the stopper member position restricting guides 95.

The metering cup 87 is provided with an electrode sensor 84 connected to ground, a fourth electrode sensor 86, and a fifth electrode sensor 85.

The fourth electrode sensor 86 is disposed above the bottom portion 90 of the metering cup 87 and in the metering cup 87. The distance between the bottom of the metering cup 87 and the fourth electrode sensor 86 corresponds to the height (level) of the base solution in the metering cup 87 charged from the chemical bottle 2. The fifth electrode sensor 85 is provided at the position higher than that of the fourth electrode sensor 86. The difference between the height (longitudinal installation position) of the fourth electrode sensor 86 and the fifth electrode sensor 85 corresponds to the height (level) of the buffer solution in the metering cup 87. Note that the base solution is charged into the metering cup 87 until the fourth electrode sensor 86 detects the base solution. Next, the buffer solution is charged from the chemical bottle 3 into the metering cup 87.

The fourth electrode sensor 86 detects a state in which the base solution is charged from the chemical bottle 2 into the metering cup 87 up to the height of the fourth electrode sensor 86. That is, the fourth electrode sensor 86 detects a state in which the base solution has reached the fourth level. The fourth electrode sensor 86 sends the obtained detection result to the controller 50. The controller 50 determines a first volume of the base solution based on the detection result.

The fifth electrode sensor 85 detects a state in which the buffer solution is charged from the chemical bottle 3 into the metering cup 87 up to the height of the fifth electrode sensor 85. That is, the fifth electrode sensor 85 detects a state in which the buffer solution has reached the fifth level higher than the fourth level. In other words, the fifth electrode sensor 85 detects a state in which the base solution and the buffer solution are stored up to the fifth level. The fifth electrode sensor 85 sends the obtained detection result to the controller 50. The controller 50 determines a second volume of the buffer solution by calculating the difference between the fifth level and the fourth level.

Figure 17:
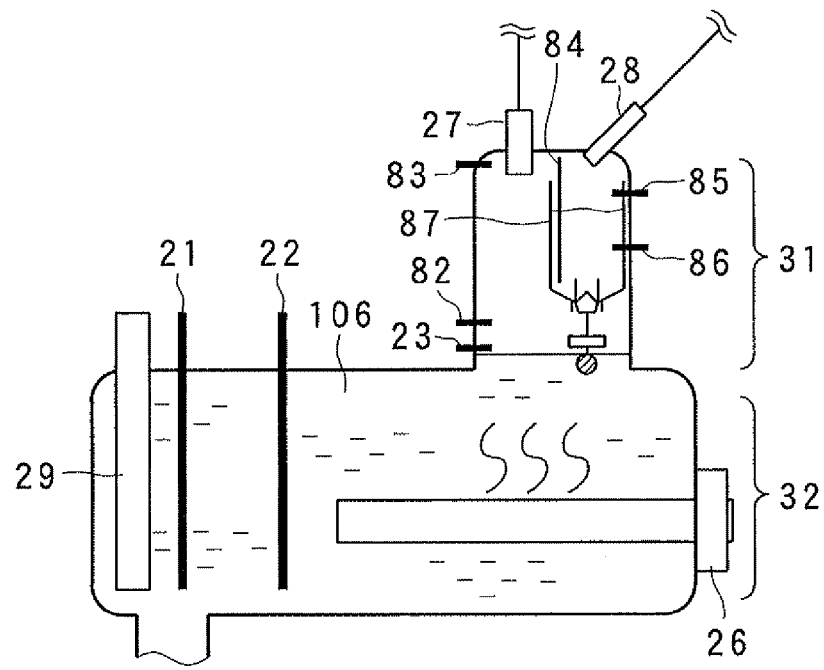
FIG. 17 is a view showing a state in which the base solution and the buffer solution are stored up to the fifth level in the metering cup shown in FIG. 11.
Figure 18:
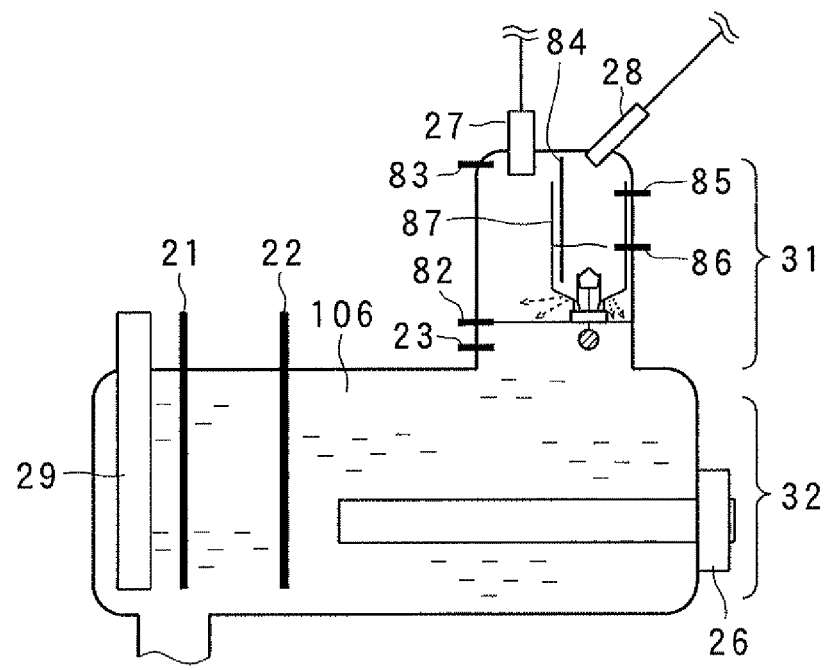
FIG. 18 is a view showing a state in which the outlet of the metering cup shown in FIG. 11 is opened.
Figure 19:
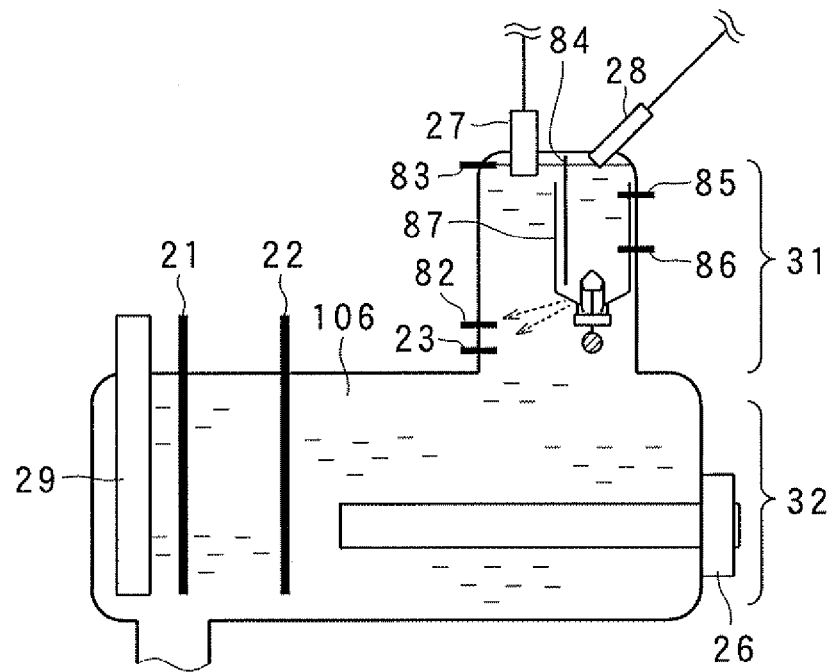
FIG. 19 is a view showing a state in which the base solution and buffer solution diluted with the dilution water are stored up to the seventh level in the dilution tank shown in FIG. 11 and the mixture of the chemicals is completed.

Next, an operation of the endoscope washer-disinfector of the second embodiment configured as described above will be described with reference to FIGS. 17 to 19. FIG. 17 shows a state in which the base solution and the buffer solution are stored up to the fifth level in the metering cup 87 shown in FIG. 11. FIG. 18 shows a state in which the outlet of the metering cup 87 shown in FIG. 11 is opened. FIG. 19 shows a state in which the base solution and buffer solution diluted with the dilution water are stored up to the seventh level in the dilution tank 106 shown in FIG. 11 and the mixture of the chemicals is completed.

Hereinafter, a process will be described in which the dilution water and both of the base solution and the buffer solution, which are chemicals to be a disinfectant solution, are charged into the dilution tank 106 of the endoscope washer-disinfector. Note that descriptions of well-known operations of the endoscope washer-disinfector will be omitted.

First, in order to mix the chemicals to prepare a disinfectant solution, the controller 50 of the endoscope washer-disinfector opens the dilution valve 7 (refer to FIG. 3). In consequence of this, the dilution water is charged from the feed-water port 27 into the dilution tank 106. As a result of the charge, as shown in FIG. 17, the dilution water is stored in the first storage portion 32 and the second storage portion 31 up to the first level which is the height of the first electrode sensor 23. Thereby, the first electrode sensor 23 sends a detection signal to the controller 50. Upon receiving the detection signal, the controller 50 sends a control signal for closing the dilution valve 7.

In this case, when the temperature sensor 22 detects a state in which the temperature of the dilution water stored in the first storage portion 32 is lower than a practical temperature of, for example, between 40° C. and 50° C., the controller 50 controls the drive of the heater 26 to heat the dilution water up to the practical temperature. Note that the dilution water may be heated up to the practical temperature before it is charged into the dilution tank 106.

Next, the controller 50 drives the pump 4 to charge the base solution stored in the chemical bottle 2 into the metering cup 87 through the chemical inlet 28. As a result of the charge, the base solution is stored in the metering cup 87 up to the fourth level which is the height of the fourth electrode sensor 86. Thereby, the fourth electrode sensor 86 sends a detection signal to the controller 50. Upon receiving the detection signal, the controller 50 sends a control signal for stopping the drive of the pump 4. In this case, the controller 50 determines a first volume of the base solution based on the detection signal.

Next, the controller 50 drives the pump 5 to charge the buffer solution stored in the chemical bottle 3 into the metering cup 87 through the chemical inlet 28. As a result of the charge, as shown in FIG. 17, the base solution and the buffer solution are stored in the metering cup 87 up to the fifth level which is the height of the fifth electrode sensor 85. Thereby, the fifth electrode sensor 85 sends a detection signal to the controller 50. Upon receiving the detection signal, the controller 50 sends a control signal for stopping the drive of the pump 5. In this case, the controller 50 determines a second volume of the buffer solution by calculating the difference between the fifth level and the fourth level. In this state, the measurement of the chemicals is completed. Note that since the outlet 96 of the metering cup 87 is closed by the stopper member 91, the volume of the chemicals in the metering cup 87 can be measured without discharging the chemicals.

Next, the controller 50 opens the dilution valve 7. In consequence of this, the dilution water is charged from the feedwater port 27 into the dilution tank 106. As a result of the charge, as shown in FIG. 18, the dilution water is stored in the second storage portion 31 up to the sixth level which is the height of the sixth electrode sensor 82. Thereby, the sixth electrode sensor 82 sends a detection signal to the controller 50.

In this case, the float member 92 floats in the dilution water stored up to the sixth level. In consequence, the stopper member 91 which has closed the outlet 96 of the metering cup 87 is raised, thereby opening the outlet 96. As a result of this, the base solution and the buffer solution in the metering cup 87 are discharged into the dilution tank 106 through the opening 99k of the retainer 99.

Next, as shown in FIG. 19, the base solution and buffer solution diluted with the dilution water are stored in the second storage portion 31 up to the seventh level which is the height of the seventh electrode sensor 83. The seventh electrode sensor 83 detects a state in which the base solution and buffer solution diluted with the dilution water have reached the level required for the preparation. The seventh electrode sensor 83 sends a detection signal to the controller 50. Upon receiving the detection signal, the controller 50 sends a control signal for closing the dilution valve 7.

In this case, as shown in FIG. 19, the metering cup 87 is immersed in the base solution and buffer solution diluted with the dilution water in the second storage portion 31. In addition, the base solution and buffer solution diluted with the dilution water, which are detected by the seventh electrode sensor 83, have been mixed to be a disinfectant solution in a predetermined concentration used for disinfecting the endoscope 190.

Next, in order to discharge the prepared disinfectant solution from the dilution tank 106, the controller 50 controls the drive of the pump 8. Thereby, the prepared disinfectant solution is supplied from the chemical outlet 29 to the washing and disinfection bath 1 through the duct 29k.

In this case, when the sixth electrode sensor 82 detects a state in which the disinfectant solution has been discharged, the controller 50 stops the drive of the pump 8. In consequence, as described above, the float member 92 floats, and the stopper member 91 is raised, thereby opening the outlet 96. As a result of this, the disinfectant solution in the metering cup 87 is discharged from the metering cup 87, thereby adjusting the level in the second storage portion 31. In this state, the apparatus is left until all the disinfectant solution in the metering cup 87 is discharged through the opening 99k of the retainer 99.

In this case, the float member position restricting guides 94 are provided around the outer circumference of the outlet 96 in the lower surface 90t of the bottom portion 90 of the metering cup 87. Therefore, even when the float member 92 floats, the float member 92 does not close the opening 99k of the retainer 99.

Finally, after all the disinfectant solution in the metering cup 87 is discharged, the controller 50 controls the drive of the pump 8 again to discharge all the disinfectant solution stored in the dilution tank 106 to the washing and disinfection bath 1.

In this case, the stopper member position restricting guides 95 are provided along the outer circumference of the outlet 96 in the upper surface 90j of the bottom portion 90 of the metering cup 87. Therefore, even when the stopper member 91 is raised, the stopper member 91 is prevented from being displaced from the outlet 96. That is, after the discharge of the disinfectant solution from the metering cup 87 is completed, the stopper member 91 tightly closes the outlet 96.

As described above, in the second embodiment, the metering cup 87 is provided in the second storage portion 31 of the dilution tank 106. In addition, in the metering cup 87, the fourth electrode sensor 86 for measuring the first volume of the base solution and the fifth electrode sensor 85 for measuring the second volume of the buffer solution are provided. That is, the volumes of the base solution and the buffer solution are measured in the metering cup 87.

According to the above configuration, even when the volume of the base solution charged into the dilution tank 106 is small, since the area of base and the volume of the metering cup 87 are smaller than those of the second storage portion 31, variation of the level in the metering cup 87 caused by charging the base solution is relatively large. Therefore, the fourth electrode sensor 86 can accurately detect the fourth level after the base solution is charged. In consequence, the first volume, which is the volume of the charged base solution, can be accurately measured with a relatively simple configuration manufactured at a low cost by using the fourth electrode sensor 86 only.

In addition, even when the volume of the buffer solution charged into the dilution tank 106 is small, since the area of base and the volume of the metering cup 87 are small, variation of the level in the metering cup 87 caused by charging the buffer solution is relatively large. Therefore, the fifth electrode sensor 85 can accurately detect the fifth level after the buffer solution is charged. In consequence, the second volume, which is the volume of the charged buffer solution, can be accurately measured with a relatively simple configuration manufactured at a low cost by using the fifth electrode sensor 85 only.

Furthermore, in the second embodiment, when the sixth electrode sensor 82 provided in the second storage portion 31 detects a state in which either the dilution water or the base solution and buffer solution diluted with the dilution water are stored up to the sixth level, the outlet 96 of the metering cup 87 opens. This is because the stopper member 91 for closing the outlet 96 is raised by the float member 92 which floats in either the dilution water or the base solution and buffer solution diluted with the dilution water.

In consequence, the base solution and buffer solution stored in the metering cup 87 can be discharged into the dilution tank 106 only by storing either the dilution water or the base solution and buffer solution diluted with the dilution water up to the sixth level. As a result of this, the base solution and buffer solution can be reliably mixed.

As described above, the endoscope washer-disinfector can be provided which accurately measures any volume of chemicals supplied to the dilution tank 106 and precisely controls the volume of the chemicals to be supplied. The apparatus has a configuration manufactured at a low cost in which only conventional electrode level sensors are disposed in the metering cup 87 of the second storage portion 31 of the dilution tank 106. That is, the configuration does not require disposing sophisticated and precise level sensors in the dilution tank 106 or the chemical bottle 2, 3 and disposing flow sensors in the ducts 2k and 3k.

In addition, employing the metering cup 87 whose volume is smaller than that of the second storage portion 31 allows any volume of chemicals supplied to the dilution tank 106 to be measured more accurately, when compared with the first embodiment.

Hereinafter, a modification example will be described. In the above described second embodiment, the stopper member 91 of the metering cup 87 opens and closes the outlet 96 by using the weight 93 and the float member 92. However, the outlet 96 may be opened and closed by using, for example, a solenoid valve.

In addition, in the above described second embodiment, the chemicals are measured by using the metering cup 87. Therefore, the second storage portion 31 may not necessarily have an area of base and a volume smaller than those of the first storage portion 32 as described in the first embodiment. Furthermore, in the above described first and second embodiments, the base solution is charged into the dilution tank before the buffer solution is charged. However, the buffer solution may be charged into the dilution tank before the base solution is charged. Note that the base solution and buffer solution diluted with the dilution water may be heated by the heater 26.

Third Embodiment

Figure 20:
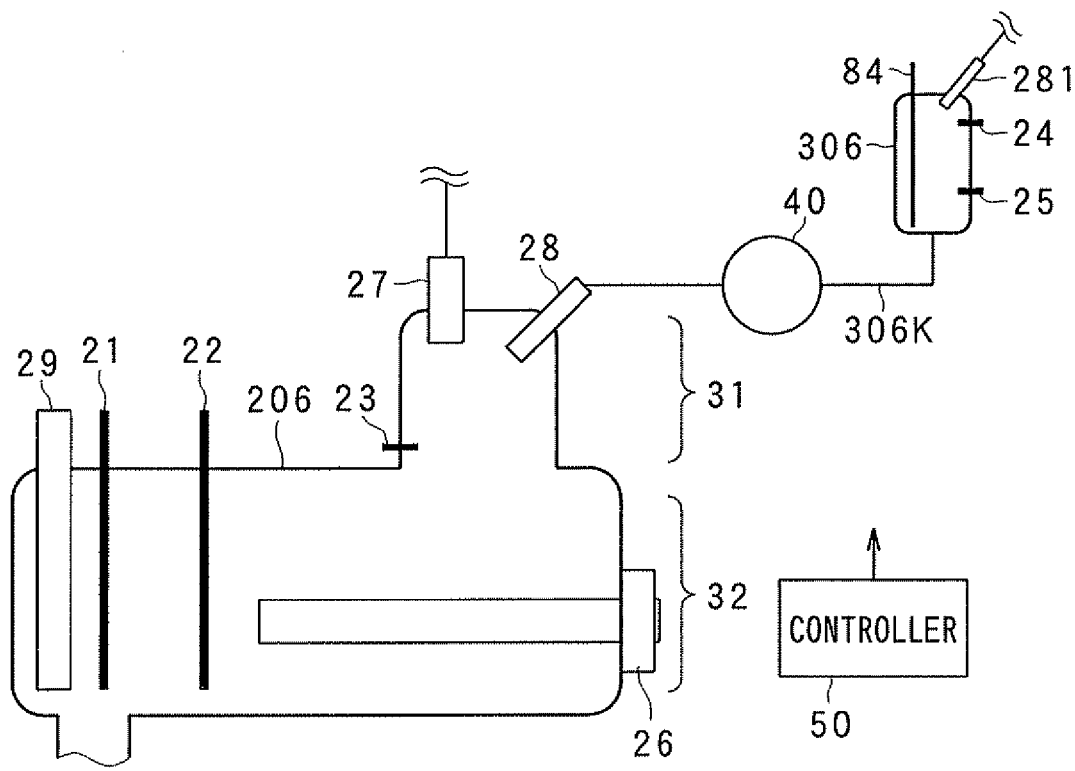
FIG. 20 is a schematic view showing configurations of a dilution tank and a reserve tank of an endoscope washer-disinfector of the third embodiment.

FIG. 20 is a schematic view showing configurations of a dilution tank and a reserve tank of an endoscope washer-disinfector of the third embodiment.

The configuration of the endoscope washer-disinfector of the third embodiment differs from that of the second embodiment shown in FIGS. 11 to 19 in that the reserve tank is provided outside the dilution tank without providing the metering cup 87. Therefore, only the difference from the first and second embodiments will be described. The same parts as those of the first and second embodiments are denoted with the same reference numerals to omit descriptions of the parts.

As shown in FIG. 20, the main part of a dilution tank 206 comprises the first storage portion 32 and the second storage portion 31. The second storage portion 31 is formed on the top of the first storage portion 32 and is communicated with the first storage portion 32. The second storage portion 31 has an area of base and a volume smaller than those of the first storage portion 32. That is, in the third embodiment, the dilution tank 206 comprises a two-stage storage portion having two different volumes.

The second storage portion 31 is provided with the above described feed-water port 27, chemical inlet 28, and first electrode sensor 23. The feed-water port 27 and the chemical inlet 28 are provided on the top of the second storage portion 31. The first electrode sensor 23 is provided in the vicinity of the position where the second storage portion 31 communicates with the first storage portion 32.

In addition, a reserve tank 306 is provided outside the dilution tank 206. The reserve tank 306 has an area of base and a volume smaller than those of the second storage portion 31. The reserve tank 306 is provided with a chemical inlet 281, the electrode sensor 84 connected to ground, the second electrode sensor 25, and the third electrode sensor 24. The reserve tank 306 is connected to the chemical inlet 28 of the second storage portion 31 through a duct 306k. A solenoid valve (or a pump) 40 is provided at the midpoint of the duct 306k. The solenoid valve 40 charges the base solution and the buffer solution (a concentrated solution) of the disinfectant solution from the reserve tank 306 into the dilution tank 206.

The chemical inlet 281 is provided on the top of the reserve tank 306. The chemical inlet 281 is connected to the ducts 2k and 3k shown in FIG. 3. The second electrode sensor 25 is disposed above the bottom of the reserve tank 306 in the reserve tank 306. The distance between the bottom of reserve tank 306 and the second electrode sensor 25 corresponds to the height (level) of the base solution in the reserve tank 306 charged from the chemical bottle 2. The third electrode sensor 24 is provided at the position higher than that of the second electrode sensor 25. The difference between the height (longitudinal installation position) of the second electrode sensor 25 and the height of the third electrode sensor 24 corresponds to the height (level) of the buffer solution in the reserve tank 306. Note that the base solution is charged into the reserve tank 306 until the second electrode sensor 25 detects the base solution. Next, the buffer solution is charged from the chemical bottle 3 into the reserve tank 306.

The second electrode sensor 25 detects a state in which the base solution is charged from the chemical bottle 2 into the reserve tank 306 up to the height of the second electrode sensor 25. That is, the second electrode sensor 25 detects a state in which the base solution has reached the second level. The second electrode sensor sends the obtained detection result to the controller 50. The controller 50 determines a first volume of the base solution based on the detection result.

The third electrode sensor 24 detects a state in which the buffer solution is charged from the chemical bottle 3 into the reserve tank 306 up to the height of the third electrode sensor 24. That is, the third electrode sensor 24 detects a state in which the buffer solution has reached the third level higher than the second level. In other words, the third electrode sensor 24 detects a state in which the base solution and the buffer solution are stored up to the third level. The third electrode sensor 24 sends the obtained detection result to the controller 50. The controller 50 determines a second volume of the buffer solution by calculating the difference between the third level and the second level.

Figure 21:
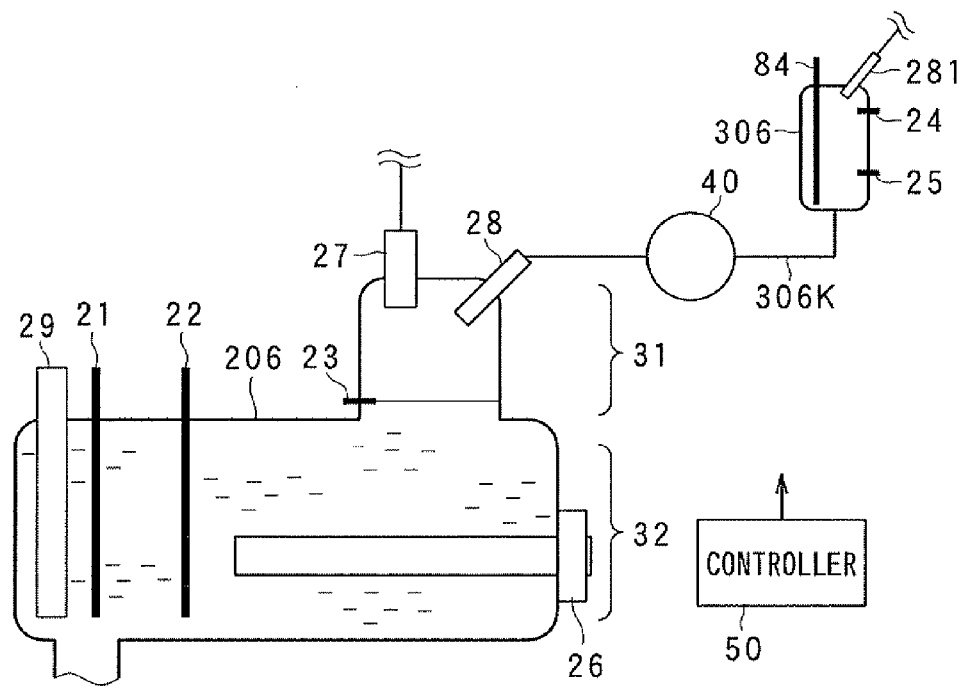
FIG. 21 is a view showing a state in which the dilution water is stored up to the first level in the dilution tank shown in FIG. 20.
Figure 22:
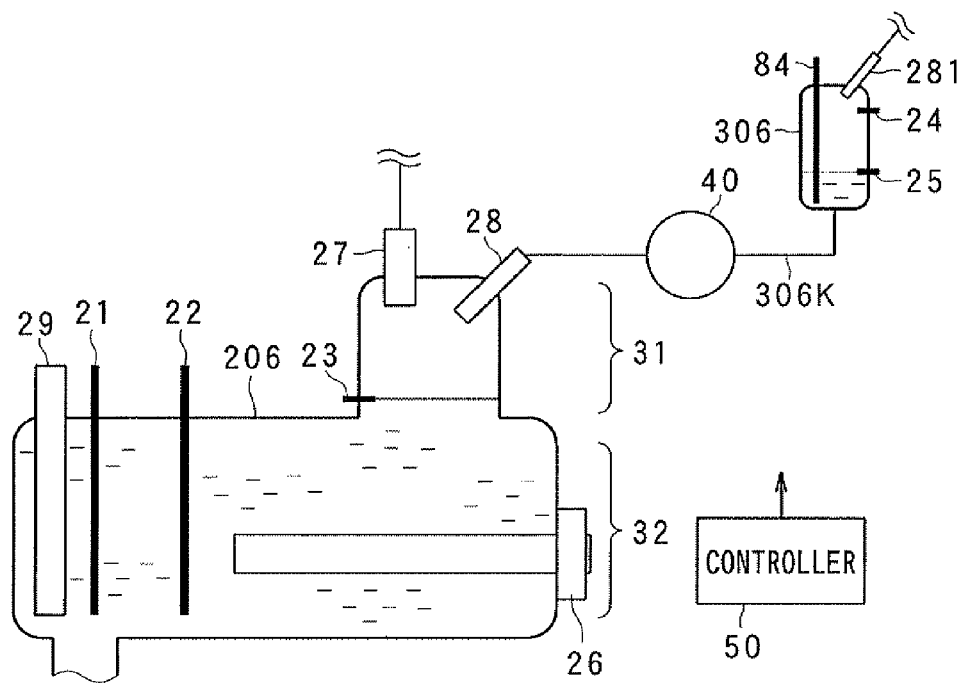
FIG. 22 is a view showing a state in which the base solution is stored up to the second level in the reserve tank shown in FIG. 20.
Figure 23:
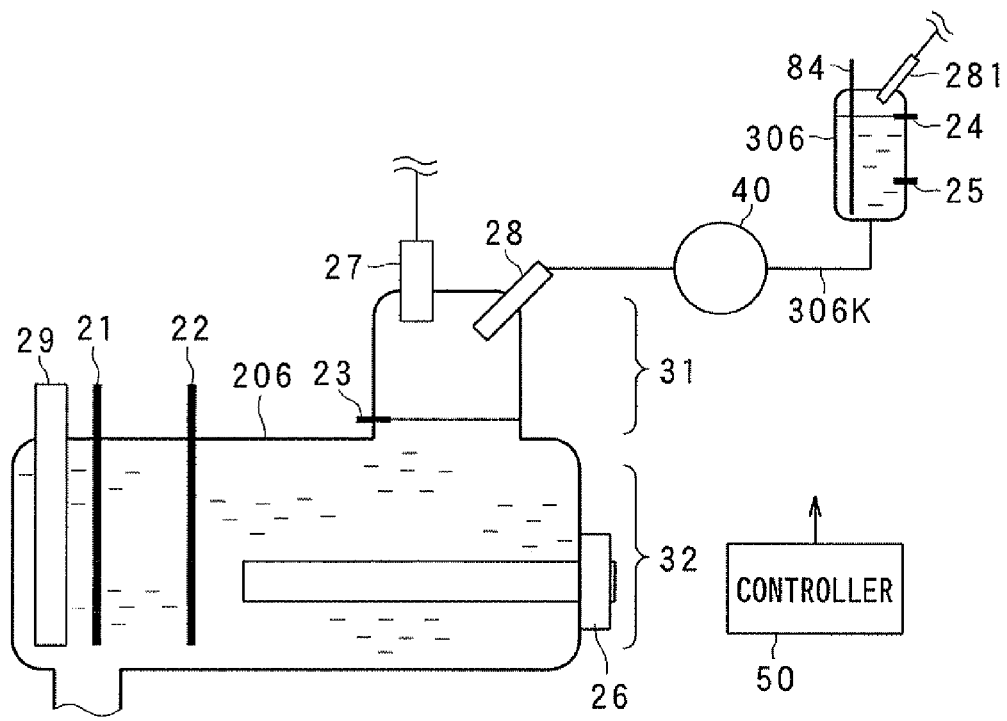
FIG. 23 is a view showing a state in which the base solution and the buffer solution are stored up to the third level in the reserve tank shown in FIG. 20.
Figure 24:
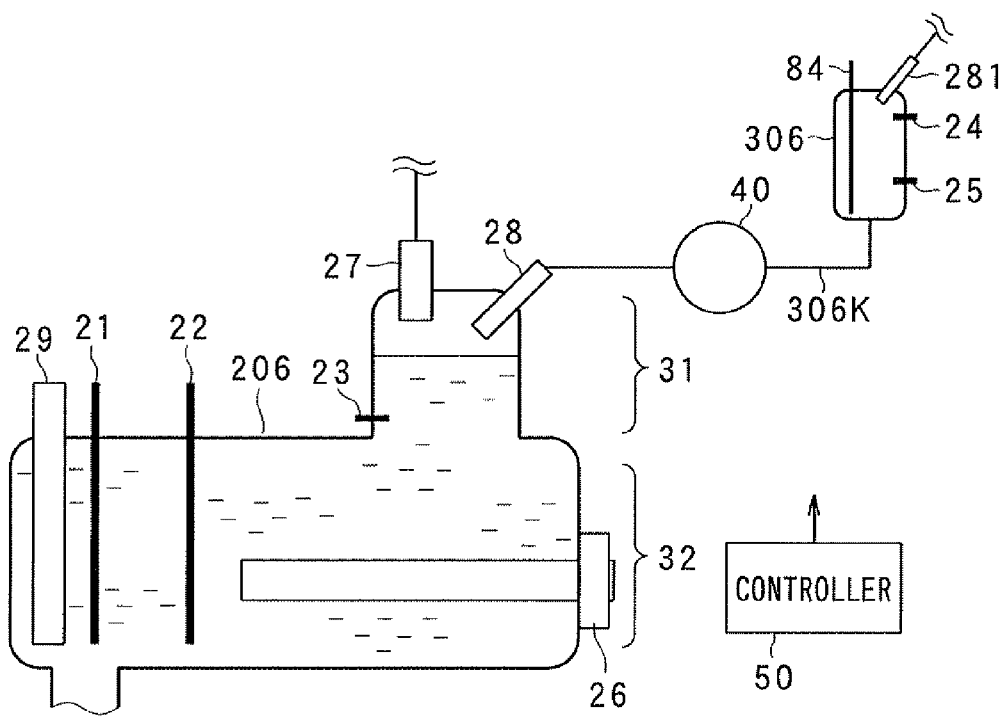
FIG. 24 is a view showing a state in which the base solution and buffer solution diluted with the dilution water are stored in the dilution tank shown in FIG. 20 and the mixture of the chemicals is completed.

Next, an operation of the endoscope washer-disinfector of the third embodiment configured as described above will be described with reference to FIGS. 21 to 24. FIG. 21 shows a state in which the dilution water is stored up to the first level in the dilution tank 206 shown in FIG. 20. FIG. 22 shows a state in which the base solution is stored up to the second level in the reserve tank 306. FIG. 23 shows a state in which the base solution and buffer solution are stored up to the third level in the reserve tank 306. FIG. 24 shows a state in which the base solution and buffer solution diluted with the dilution water are stored in the dilution tank 206 and the mixture of the chemicals is completed.

Hereinafter, a process will be described in which the dilution water and both of the base solution and buffer solution, which are chemicals to be a disinfectant solution, are charged into the dilution tank 206 of the endoscope washer-disinfector. Note that descriptions of well-known operations of the endoscope washer-disinfector will be omitted.

First, in order to mix the chemicals to prepare a disinfectant solution, the controller 50 of the endoscope washer-disinfector opens the dilution valve 7 (refer to FIG. 3). In consequence of this, the dilution water such as tap water is charged from the feed-water port 27 into the dilution tank 206. As a result of the charge, as shown in FIG. 21, the dilution water is stored in the first storage portion 32 and the second storage portion 31 up to the first level which is the height of the first electrode sensor 23. Thereby, the first electrode sensor 23 sends a detection signal to the controller 50. Upon receiving the detection signal, the controller 50 sends a control signal for closing the dilution valve 7.

Next, the controller 50 drives the pump 4 to charge the base solution stored in the chemical bottle 2 into the reserve tank 306 through the chemical inlet 281. As a result of the charge, as shown in FIG. 22, the base solution is stored in the reserve tank 306 up to the second level which is the height of the second electrode sensor 25. Thereby, the second electrode sensor 25 sends a detection signal to the controller 50. Upon receiving the detection signal, the controller 50 sends a control signal for stopping the drive of the pump 4. In this case, the controller 50 determines a first volume of the base solution based on the detection signal.

Next, the controller 50 drives the pump 5 to charge the buffer solution stored in the chemical bottle 3 into the reserve tank 306 through the chemical inlet 281. As a result of the charge, as shown in FIG. 23, the base solution and the buffer solution are stored up to the third level which is the height of the third electrode sensor 24. Thereby, the third electrode sensor 24 sends a detection signal to the controller 50. Upon receiving the detection signal, the controller 50 so sends a control signal for stopping the drive of the pump 5. In this case, the controller 50 determines a second volume of the buffer solution by calculating the difference between the third level and the second level.

Next, the controller 50 drives the solenoid valve (or a pump) 40 to charge the base solution and the buffer solution stored in the reserve tank 306 into the second storage portion 31. As a result of the charge, as shown in FIG. 24, the base solution and buffer solution diluted with the dilution water are stored in the dilution tank 206. Note that the base solution and buffer solution diluted with the dilution water are mixed to be a disinfectant solution in a predetermined concentration used for disinfecting the endoscope 190.

Finally, the controller 50 controls the drive of the pump 8 to supply the disinfectant solution in a predetermined concentration from the chemical outlet 29 to the washing and disinfection bath 1 through the duct 29k.

As described above, in the third embodiment, the reserve tank 306 is provided outside the dilution tank 206. In addition, the second electrode sensor 25 for measuring the first volume of the base solution and the third electrode sensor 24 for measuring the second volume of the buffer solution are provided in the reserve tank 306. That is, the volumes of the base solution and the buffer solution are measured in the reserve tank 306.

According to the above configuration, even when the volume of the base solution charged into the reserve tank 306 is small, since the area of base and the volume of the reserve tank 306 are smaller than those of the second storage portion 31, variation of the level in the reserve tank 306 caused by charging the base solution is relatively large. Therefore, the second electrode sensor 25 can accurately detect the second level after the base solution is charged. In consequence, the first volume, which is the volume of the charged base solution, can be accurately measured with a relatively simple configuration manufactured at a low cost by using the second electrode sensor 25 only.

In addition, even when the volume of the buffer solution charged into the reserve tank 306 is small, since the area of base and the volume of the reserve tank 306 are smaller than those of the second storage portion 31, variation of the level in the reserve tank 306 caused by charging the buffer solution is relatively large. Therefore, the third electrode sensor 24 can accurately detect the third level after the buffer solution is charged. In consequence, the second volume, which is the volume of the charged buffer solution, can be accurately measured with a relatively simple configuration manufactured at a low cost by using the third electrode sensor 24 only.

In addition, in the dilution tank 206, the level of the dilution water is adjusted in the second storage portion 31, which is the upper-stage storage portion having a smaller area of base, by using the first electrode sensor 23. In this case, since variation of the level of the dilution water in the second storage portion 31 is relatively large, adjustment errors become small.

In addition, the volumes of the base solution and the buffer solution for one-time use are smaller than that of the dilution water. Therefore, since the area of base of the reserve tank 306 is smaller than that of the second storage portion 31 of the dilution tank 206, variations of the levels of the base solution and the buffer solution in the reserve tank 306 become relatively large and errors in the volumes become small.

As described above, the endoscope washer-disinfector can be provided which accurately measures any volume of chemicals supplied to the dilution tank 206 and precisely controls the volume of the chemicals to be supplied. The apparatus has a configuration manufactured at a low cost in which only conventional electrode level sensors are disposed in the reserve tank 306 outside the dilution tank 206. That is, the configuration does not require disposing sophisticated and precise level sensors in the dilution tank 206 or the chemical bottles 2, 3 and disposing flow sensors in the ducts 2k and 3k.

In addition, employing the reserve tank 306 whose volume is smaller than that of the second storage portion 31 allows any volume of chemicals supplied to the dilution tank 206 to be measured more accurately, when compared with the first embodiment. Furthermore, the base solution and the buffer solution (a concentrated solution), which are chemicals, are measured alone in the reserve tank 306. Therefore, the volumes of the base solution and the buffer solution can be accurately measured, regardless of adjustment errors of the level of the dilution water in the dilution tank 206. In addition, since the dilution water and both of the base solution and the buffer solution are measured in the dilution tank 206 and the reserve tank 306, respectively, the dilution water can be heated alone in the dilution tank 206 as in the first embodiment. Note that the base solution and buffer solution diluted with the dilution water may be heated by the heater 26.

According to the embodiments of the present invention, an apparatus for washing and disinfecting an endoscope can be provided which has a relatively simple configuration manufactured at a low cost, accurately measures any volume of chemicals supplied to a dilution tank, and precisely controls the volume of the chemicals to be supplied.

As described above in detail, according to the embodiments of the present invention, configurations described below are obtained.

(1) An apparatus for washing and disinfecting an endoscope, which prepares a chemical for disinfecting the endoscope in a dilution tank provided in a main body thereof, comprising:

a chemical inlet through which a concentrated chemical is charged from a chemical bottle via a chemical supply duct;

a dilution water inlet through which the dilution water is charged via a water supply duct;

a chemical supplying means provided in the chemical supply duct;

a switching means which starts and stops supplying the dilution water via the water supply duct; and a detecting means which detects the volume of the chemical stored in the dilution tank;

wherein the dilution tank comprises a two-stage storage portion having two different areas of base and volumes.

(2) The apparatus according to (1), further comprising a metering cup provided in the dilution tank, the metering cup measuring the volume of the chemical.

(3) The apparatus according to (2), wherein a bottom portion of the metering cup is provided with an outlet and a stopper closing the outlet.

(4) The apparatus according to (3), wherein the stopper is connected to a float member and a weight, and when the level in the dilution tank is in a state where the float member does not float, the stopper is pulled downward by the weight to close the outlet, and when the level in the dilution tank is in a state where the float member floats, the stopper is raised upward to open the outlet.

(5) The apparatus according to (4), wherein the outlet has a plurality of stopper position restricting guides along an outer circumference thereof to prevent displacement of the stopper.

(6) The apparatus according to (5), further comprising a float member position restricting guide which prevents the float member from closing the outlet when the level is raised in the dilution tank.

(7) The apparatus according to (6), wherein the length of the stopper position restricting guides is determined so that the stopper falls inside the stopper position restricting guides when the float member is raised up to the position of the float member position restricting guide.

(8) The apparatus according to (7), wherein the dilution water is heated when the level in the metering cup is in a state where the chemical is not discharged, the dilution water is charged when a predetermined volume of the chemical is stored in the metering cup, and the dilution water dilutes the chemical to a proper concentration when the chemical stored in the metering cup is discharged.

(9) The apparatus according to (1), wherein the dilution water is charged into a lower storage portion of the dilution tank having larger area of base and volume and is heated, and the volume of the chemical is measured based on variation of the level when the chemical is charged into an upper storage portion having smaller area of base and volume.

(10) The apparatus according to (8), wherein the float member connected to the stopper of the metering cup is disposed in an upper storage portion of the dilution tank and is raised as the dilution water is charged, thereby opening the outlet to discharge the chemical stored in the metering cup.

It will be appreciated that the present invention is not limited to the configurations described above, but any and all modifications, variations or equivalents, which may occur to those who are skilled in the art, should be considered to fall within the scope of the present invention.

What is claimed is:

1. An apparatus for washing and disinfecting an endoscope comprising:
   a dilution tank into which first and second chemicals and dilution water are charged in a filling direction, the dilution tank diluting the first and second chemicals to a predetermined concentration to be used for disinfecting the endoscope, and the dilution tank including:
     a first storage portion;
     a second storage portion which has an area of base smaller than an area of base of the first storage portion, has a volume smaller than a volume of the first storage portion, and communicates with the first storage portion;
     a first electrode sensor that is provided adjacent to where the second storage portion communicates with the first storage portion, and detects a state in which the dilution water is charged into the second storage portion up to a first level;
     a second electrode sensor that is provided at a position higher in the filling direction than the position of the first electrode sensor, and detects a state in which the first chemical is charged into the second storage portion up to a second level; and
     a third electrode sensor that is provided at a position higher in the filling direction than the position of the second electrode sensor, and detects a state in which the second chemical is charged into the second storage portion up to a third level; and
   a measurement unit which measures, as a first volume, a volume of the first chemical based on a detection result of the second electrode sensor and measures, as a second volume, a volume of the second chemical based on a detection result of the third electrode sensor and the detection result of the second electrode sensor.

2. The apparatus according to claim 1, wherein the second storage portion is formed on a top of the first storage portion.

3. The apparatus according to claim 1, wherein the first storage portion includes a heating member which heats either the dilution water or the first and second chemicals diluted with the dilution water.

* * * * *